United States Patent
Jung et al.

(10) Patent No.: US 11,157,095 B2
(45) Date of Patent: Oct. 26, 2021

(54) ELECTRONIC STYLUS INCLUDING A PLURALITY OF BIOMETRIC SENSORS AND OPERATING METHOD THEREOF

(71) Applicant: Samsung Electronics Co., Ltd., Gyeonggi-do (KR)

(72) Inventors: Sun Ok Jung, Gyeonggi-do (KR); Dongwook Kim, Seoul (KR); Minjung Kim, Gyeongsangnam-do (KR); Sookjin Kim, Gyeonggi-do (KR); Jin-Gil Yang, Gyeonggi-do (KR); Inji Jin, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/724,805

(22) Filed: Dec. 23, 2019

(65) Prior Publication Data
US 2020/0125190 A1 Apr. 23, 2020

Related U.S. Application Data

(63) Continuation of application No. 15/240,241, filed on Aug. 18, 2016, now abandoned.

(30) Foreign Application Priority Data

Oct. 21, 2015 (KR) .................. 10-2015-0146651

(51) Int. Cl.
*G06F 3/0354* (2013.01)
*G16H 10/65* (2018.01)
(Continued)

(52) U.S. Cl.
CPC ........ *G06F 3/03545* (2013.01); *A61B 5/0205* (2013.01); *A61B 5/0245* (2013.01);
(Continued)

(58) Field of Classification Search
CPC ... A61B 5/6898; A61B 5/7275; A61B 5/0245; A61B 5/0205; A61B 5/01; A61B 5/024;
(Continued)

(56) References Cited

U.S. PATENT DOCUMENTS

2009/0264713 A1   10/2009   Van Loenen et al.
2011/0301435 A1   12/2011   Albert et al.
(Continued)

FOREIGN PATENT DOCUMENTS

JP      2009-532239 A     9/2009
KR   10-2011-0008434 A    1/2011

*Primary Examiner* — Yaron Cohen
(74) *Attorney, Agent, or Firm* — Cha & Reiter, LLC

(57) ABSTRACT

An electronic device, accessory device and method using the same are disclosed herein. The accessory device is stowable in the electronic device, and includes at least a first sensor, a second sensor, a communication interface and a processor. The method includes receiving, through the communication interface, information from the electronic device corresponding to an application executed in the electronic device, in response to the received information, obtaining the first data through the first sensor when the received information is a first information and obtaining the second data through the second sensor when the information is a second information, and transmitting, to the electronic device, data based on at least one of the first data and the second data.

16 Claims, 20 Drawing Sheets

(51) Int. Cl.
*A61B 5/00* (2006.01)
*A61B 5/0245* (2006.01)
*A61B 5/0205* (2006.01)
*G06F 3/01* (2006.01)
*G16H 40/63* (2018.01)
*G06F 1/26* (2006.01)
*G06F 3/038* (2013.01)
*G16H 50/20* (2018.01)
*A61B 5/01* (2006.01)
*A61B 5/11* (2006.01)
*A61B 5/021* (2006.01)
*A61B 5/024* (2006.01)
*A61B 5/318* (2021.01)

(52) U.S. Cl.
CPC .......... *A61B 5/6898* (2013.01); *A61B 5/7275* (2013.01); *G06F 1/26* (2013.01); *G06F 3/015* (2013.01); *G06F 3/0383* (2013.01); *G16H 10/65* (2018.01); *G16H 40/63* (2018.01); *G16H 50/20* (2018.01); *A61B 5/01* (2013.01); *A61B 5/021* (2013.01); *A61B 5/024* (2013.01); *A61B 5/1112* (2013.01); *A61B 5/1118* (2013.01); *A61B 5/318* (2021.01)

(58) Field of Classification Search
CPC ..... A61B 5/0402; A61B 5/1112; A61B 5/021; A61B 5/1118; G16H 10/65; G16H 50/20; G16H 40/63; G06F 1/26; G06F 3/015; G06F 3/0416; G06F 3/0383; G06F 3/03545
See application file for complete search history.

(56) References Cited

U.S. PATENT DOCUMENTS

| | | | |
|---|---|---|---|
| 2013/0181953 A1* | 7/2013 | Hinckley | G06F 3/03545 345/179 |
| 2014/0029182 A1* | 1/2014 | Ashcraft | G06F 3/03545 361/679.4 |
| 2014/0180481 A1* | 6/2014 | Park | G06F 3/03545 700/275 |
| 2014/0253469 A1 | 9/2014 | Hicks et al. | |
| 2016/0179222 A1* | 6/2016 | Chang | G06F 3/0383 345/179 |
| 2016/0228064 A1 | 8/2016 | Jung et al. | |

* cited by examiner

ELECTRONIC STYLUS INCLUDING A PLURALITY OF BIOMETRIC SENSORS AND OPERATING METHOD THEREOF

CROSS-REFERENCE TO RELATED APPLICATION

This application is a Continuation of U.S. patent application Ser. No. 15/240,241 filed on Aug. 18, 2016 which under 35 U.S.C. § 119(a) to Korean Application Ser. No. 10-2015-0146651, which was filed in the Korean Intellectual Property Office on Oct. 21, 2015, the entire content of which is hereby incorporated by reference.

TECHNICAL FIELD

The present disclosure relates to an electronic device, and, more particularly, to an electronic device including a sensor and an operation method thereof.

BACKGROUND

Recently, electronic devices have been developed in various forms, such as a portable device (e.g., a smart phone, a tablet PC, or the like) and a wearable device (e.g., a smart watch, a head mounted device, or the like). The various electronic devices may provide various services and additional functions. For example, health information, such as heartbeats or the like, may be obtained or otherwise detected with the aid of a smart phone or a smart watch. Also, the smart phone or the smart watch may provide health services using the obtained health information.

The phenomenon has improved the effective value of an electronic device, and better satisfied various demands of users. The various demands of users may be connected to the development of various accessory devices, which may operate by interworking with the electronic device. Recently, there has been increased focus on health monitoring due to aging, and the improvement of economic conditions. Users desire to check up their health conditions without visiting a hospital or health center. Therefore, the user demand has increased for an accessory device that is capable of providing the function in real time.

SUMMARY

According to some embodiments of the disclosure, an electronic device (e.g., an accessory device) includes a limited number of sensors. In this instance, when a user checks up the health condition of the user using the electronic device (e.g., the accessory device), the user may use a different electronic device (e.g., the accessory device) for each item that the user desires to check upon (for example, blood pressure, blood sugar, body temperature, and the like), which is cumbersome.

According to some embodiments of the disclosure, to obtain one of a plurality of pieces of data, which are obtainable through a plurality of sensors included in an external electronic device, an electronic device may directly request one of the plurality of pieces of data from the external electronic device. Accordingly, a user may directly select the utilized data in the electronic device, so as to request the data from the external electronic device, which is inconvenient for the user.

According to various embodiments of the present disclosure, sensing information (e.g., biometric information) of a user, which is associated with an application that is currently executed in an electronic device, may be obtained using an external electronic device (e.g., a stylus pen) that is equipped with a plurality of sensors, and the obtained biometric information may be provided.

According to various embodiments of the present disclosure, an electronic device is provided, including a first sensor to obtain first data, a second sensor to obtain second data, a communication interface, and a processor configured to perform: receiving, through the communication interface, information from an external electronic device corresponding to an application executed in the external electronic device, in response to the received information, obtaining the first data through the first sensor when the received information is a first information and obtaining the second data through the second sensor when the information is a second information, and transmitting, to the external electronic device, data based on at least one of the first data and the second data.

According to various embodiments of the present disclosure, an electronic device is provided, including a communication interface, a processor configured to perform: determining an application executed in the electronic device, when the application is determined to be a first application, transmitting first information corresponding to the first application to an accessory device that includes a first sensor and a second sensor, through the communication interface, when the application is determined to be a second application, transmitting second information corresponding to the second application to the accessory device, through the communication interface, and receiving, from the accessory device, data obtained through one of the first sensor and the second sensor, which corresponds to one of the transmitted first information and the second information.

According to various embodiments of the present disclosure, an operation method in an electronic device is disclosed, including: receiving, from an external electronic device, information corresponding to an application executed by the external electronic device, obtaining first data through a first sensor when the received information is first information, obtaining second data through a second sensor when the received information is second information, and transmitting, to the external electronic device, data based on the first data and the second data.

As described above, an electronic device and an operation method thereof according to the present disclosure, may obtain, through a sensor, data (e.g., biometric information of a user) associated with an application that is currently executed in the electronic device, and may provide the same to the user. The biometric information may be obtained using, for example, an external electronic device (e.g., a stylus pen) equipped with a plurality of sensors. The method may decrease inconvenience caused by collecting biometric information, and may improve the user's convenience.

BRIEF DESCRIPTION OF THE DRAWINGS

The above and other aspects and features of the present disclosure will be more apparent from the following detailed description taken in conjunction with the accompanying drawings, in which.

DETAILED DESCRIPTION

Figure 1:
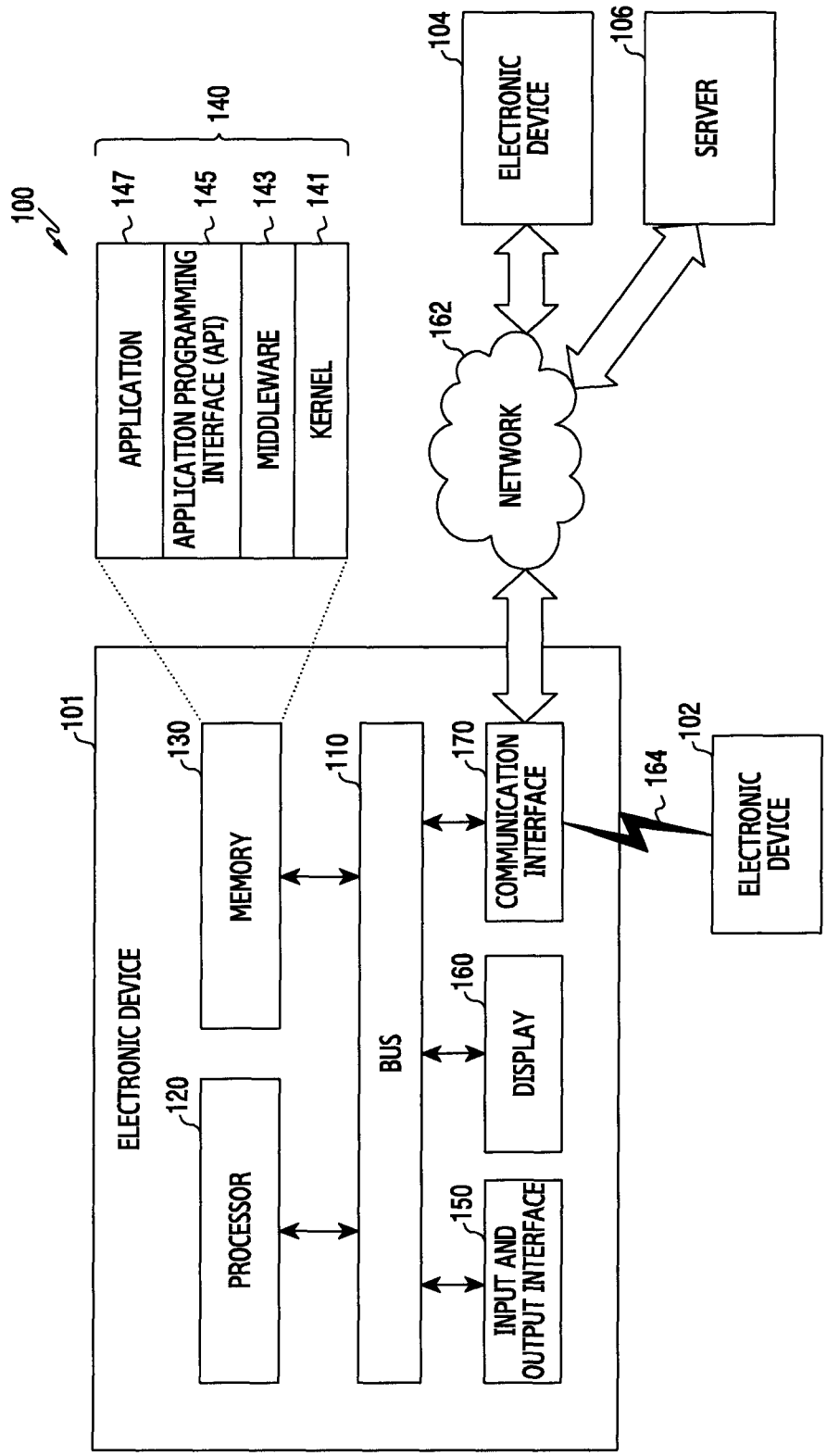
FIG. 1 is a diagram illustrating a network environment including an electronic device according to an embodiment of the present disclosure.

Hereinafter, example embodiments of the present disclosure will be described in detail with reference to the accompanying drawings. Detailed descriptions of well-known functions and structures incorporated herein may be omitted to avoid obscuring the subject matter of the present disclosure. Further, the terms used herein are defined in consideration of functions of the present disclosure and may vary depending on a user's or an operator's intension and usage. Therefore, the terms used herein should be understood based on the descriptions made herein. In the present disclosure, an expression such as "A or B," "at least one of A or/and B," or "one or more of A or/and B" may include all possible combinations of together listed items. Expressions such as "first," "second," "primarily," or "secondary," used in various example embodiments may represent various elements regardless of order and/or importance and do not limit corresponding elements. The expressions may be used for distinguishing one element from another element. When it is described that an element (such as a first element) is "(operatively or communicatively) coupled" to or "connected" to another element (such as a second element), the element can be directly connected to the other element or can be connected through the other element such as a third element).

An expression "configured to (or set)" used in the present disclosure may be replaced with, for example, "suitable for," "having the capacity to," "designed to," "adapted to," "made to," or "capable of" according to a situation. A term "configured to (or set)" does not always mean only "specifically designed to" by hardware. Alternatively, in some situation, an expression "apparatus configured to" may mean that the apparatus "can" operate together with another apparatus or component. For example, a phrase "a processor configured (Or set) to perform A, B, and C" may be a generic-purpose processor (such as a Central Processing Unit (CPU) or an application processor) that can perform a corresponding operation by executing at least one software program stored at an exclusive processor (such as an embedded processor) for performing a corresponding operation or at a memory device.

An electronic device according to various example embodiments of the present disclosure can include, for example, at least one of a smart phone, a tablet Personal Computer (PC), a mobile phone, a video phone, an e-book reader, a desktop PC, a laptop PC, a netbook computer, a workstation, a sever, a Personal Digital Assistant (PDA), a Portable Multimedia Player (PMP), an MPEG 3 (MP3) player, a mobile medical equipment, a camera, and a wearable device. The wearable device can include at least one of an accessory type (e.g., a watch, a ring, a bracelet, an ankle bracelet, a necklace, glasses, a contact lens, or a Head-Mounted-Device (HMD)), a fabric or clothing embedded type (e.g., electronic garments), a body attachable type (e.g., a skin pad or a tattoo), and an implantable circuit. The electronic device can include at least one of, for example, a television, a Digital Video Disk (DVD) player, an audio device, a refrigerator, an air-conditioner, a cleaner, an oven, a microwave oven, a washing machine, an air cleaner, a set-top box, a home automation control panel, a security control panel, a media box (such as Samsung HomeSync™, Apple TV™, or Google TV™), a game console (such as Xbox™, PlayStation™), an electronic dictionary, an electronic key, a camcorder, and an electronic frame.

In another embodiment, the electronic device can include at least one of various medical devices (such as various portable medical measuring devices (a blood sugar measuring device, a heartbeat measuring device, a blood pressure measuring device, or a body temperature measuring device), a Magnetic Resonance Angiography (MRA) device, a Magnetic Resonance Imaging (MRI) device, a Computed Tomography (CT) device, a scanning machine, and an ultrasonic wave device), a navigation device, a Global Navigation Satellite System (GNSS), an Event Data Recorder (EDR), a Flight Data recorder (FDR), a vehicle infotainment device, an electronic equipment for ship (such as a navigation device for ship and gyro compass), avionics, a security device, a head unit for a vehicle, an industrial or home robot, a drone, an Automatic Teller's Machine (ATM) of a financial institution, a point of sales (POS) of a store, and Internet of things (such as a bulb, various sensors, a sprinkler device, a tire alarm, a thermostat, a street light, a toaster, a sports equipment, a hot water tank, a heater, and a boiler). According to an embodiment, the electronic device can include at least one of a portion of furniture, building/construction or vehicle, an electronic board, an electronic signature receiving device, a projector, and various measuring devices (such as water supply, electricity, gas, or electric wave measuring device). An electronic device according to an embodiment is a flexible electronic device or a combination of two or more of the foregoing various devices. An electronic device according to an embodiment of the present disclosure is not limited to the foregoing devices and includes a new electronic device according to technical development. In this specification, the term "user" can refer to a person using an electronic device or a device using an electronic device (e.g., an artificial intelligent electronic device).

Referring to FIG. 1, an electronic device 101 may be part of a configuration 100, operating in communication with a network 162. The electronic device 101 may include a bus 110, a processor 120, a memory 130, an input/output interface 150, a display 160, and a communication interface 170. The electronic device 101 may omit at least one of the components or further include another component. The bus 110 can include a circuit for connecting the components 110 to 170 and delivering communication signals (e.g., control messages or data) therebetween. The processor 120 can include one or more of a central processing unit, an application processor, and a Communication Processor (CP). The processor 120, for example, can perform an operation or data processing on control and/or communication of at least another component of the electronic device 101.

The memory 130 can include a volatile and/or nonvolatile memory. The memory 130, for example, can store commands or data relating to at least another component of the electronic device 101. According to an embodiment, the memory 130 can store software and/or a program 140. The program 140, for example, can include a kernel 141, middleware 143, an Application Programming Interface (API) 145, and/or an application program (or "application") 147. At least part of the kernel 141, the middleware 143, or the API 145 can be called an Operating System (OS). The kernel 141 can control or manage system resources (e.g., the bus 110, the processor 120, or the memory 130) used for performing operations or functions implemented by the other programs (e.g., the middleware 134, the API 145, or the application program 147). Additionally, the kernel 141 can provide an interface for controlling or managing system resources by accessing an individual component of the electronic device 101 from the middleware 143, the API 145, or the application program 147.

The middleware 143, for example, can serve as an intermediary role for exchanging data between the API 145 or the application program 147 and the kernel 141 through communication. Additionally, the middleware 132 can process one or more job requests received from the application program 147, based on their priority. For example, the middleware 143 can assign a priority for using a system resource (e.g., the bus 110, the processor 120, or the memory 130) of the electronic device 101 to at least one of the application programs 147, and process the one or more job requests. The API 145, as an interface through which the application 147 controls a function provided from the kernel 141 or the middleware 143, can include, for example, at least one interface or function (e.g., an instruction) for file control, window control, image processing, or character control. The input/output interface 150, for example, can deliver commands or data inputted from a user or another external device to another component(s) of the electronic device 101, or output commands or data inputted from another component(s) of the electronic device 101 to a user or another external device.

The display 160, for example, can include a Liquid Crystal Display (LCD), a Light Emitting Diode (LED) display, an Organic Light Emitting Diode (OLED) display, a MicroElectroMechanical Systems (MEMS) display, or an electronic paper display. The display 160, for example, can display various contents (e.g., texts, images, videos, icons, and/or symbols) to the user. The display 160 can include a touch screen, for example, and receive touch, gesture, proximity, or hovering inputs by using an electronic pen or a user's body part. The communication interface 170, for example, can set a communication 164 between the electronic device 101 and an external device 102 (e.g., a first external electronic device 102, a second external electronic device 104, or a server 106). For example, the communication interface 170 can communicate with the external device (e.g., the second external electronic device 104 or the server 106) over the network 162 through wireless communication or wired communication.

The wireless communication, for example, can at least one of Long Term Evolution (LTE), LTE-Advanced (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. The wireless communication can include, for example, at least one of Wireless Fidelity (WiFi), Bluetooth, Bluetooth Low Energy (BLE), Zigbee, Near Field Communication (NFC), magnetic secure transmission, Radio Frequency (RF), and Body Area Network (BAN). The wireless communication can include GNSS. The GNSS can include, for example, Global Positioning System (GPS), Global Navigation Satellite System (GLONASS), Beidou navigation satellite system (Beidou), or Galileo (the European global satellite-based navigation system). Hereafter, the GPS can be interchangeably used with the GNSS. The wired communication, for example, can include at least one of Universal Serial Bus (USB), High Definition Multimedia Interface (HDMI), Recommended Standard 232 (RS-232), power line communications, and Plain Old Telephone Service (POTS). The network 162 can include at least one of telecommunications networks such as computer network (e.g., LAN or WAN), Internet, and telephone network.

Each of the First and second external electronic devices 102 and 104 can be the same or different type of the electronic device 101. According to various embodiments, all or part of operations executed in the electronic device 101 can be executed by another or a plurality of electronic devices (e.g., the electronic device 102 or 104 or the server 106). When the electronic device 101 is to perform a function or service automatically or at the request, instead of performing the function or the service by the electronic device 101 or additionally, the electronic device 101 can request at least part of a function relating thereto from another device (e.g., the electronic device 102 or 104, or the server 106). The other electronic device (e.g., the electronic device 102 or 104, or the server 106) can perform the requested function or an additional function and deliver its result to the electronic device 101. The electronic device 101 can provide the requested function or service by processing the received result as it is or additionally. For doing so, for example, cloud computing, distributed computing, or client-server computing techniques can be used.

Figure 2:
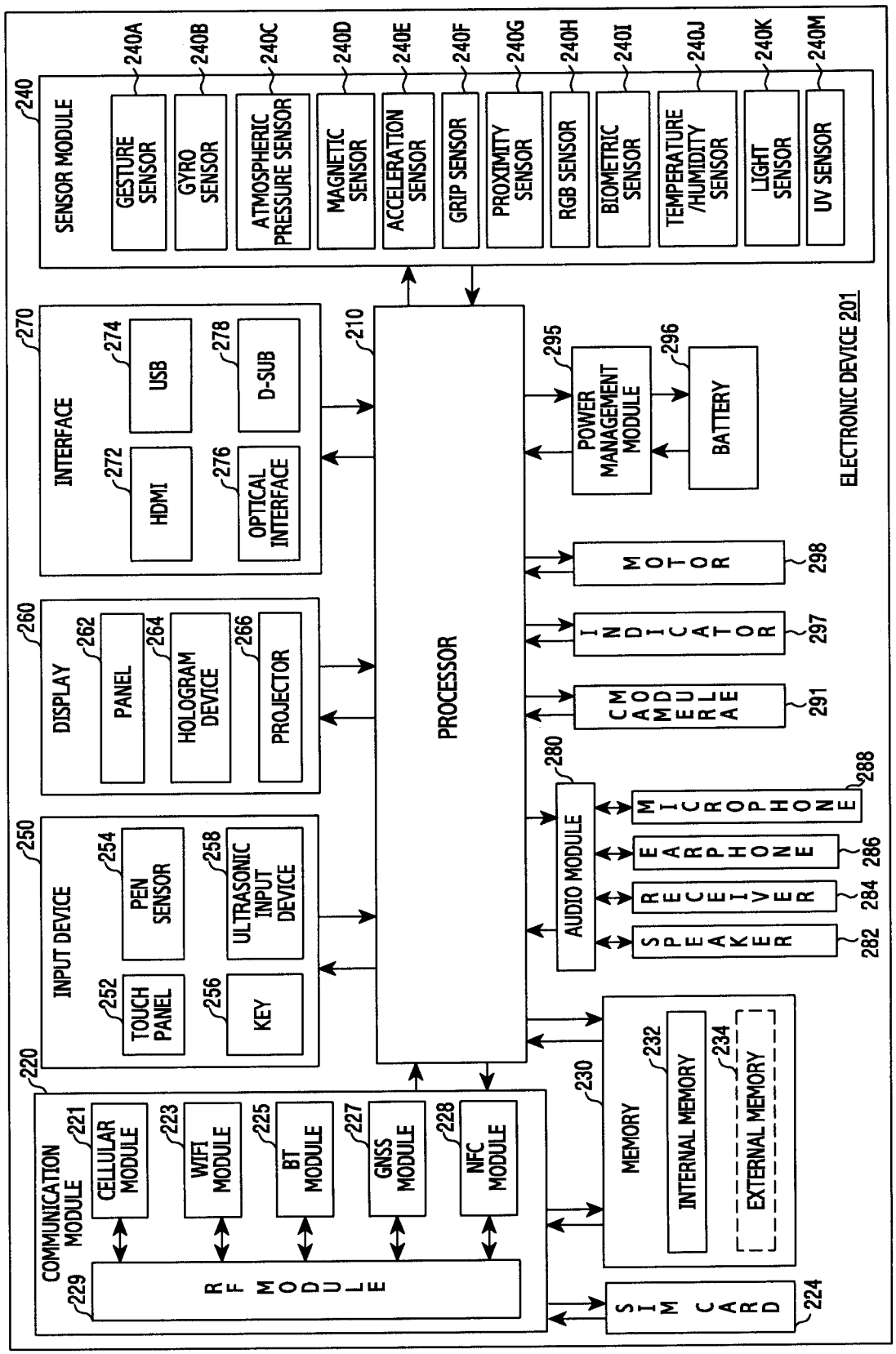
FIG. 2 is a block diagram of an electronic device according to an embodiment of the present disclosure.

FIG. 2 is a block diagram of an electronic device 201 according to various embodiments of the present disclosure. The electronic device 201, for example, can include all or part of the above-mentioned electronic device 101 shown in FIG. 1. The electronic device 201 can include one or more processors (e.g., an Application Processor (AP)) 210, a communication module 220, a Subscriber identification Module (SIM) card 224, a memory 230, a sensor module 240, an input device 250, a display 260, an interface 270, an audio module 280, a camera module 291, a power management module 295, a battery 296, an indicator 297, and a motor 298. The processor 210, for example, can control a plurality of hardware or software components connected to the processor 210 and also perform various data processing and operations by executing an operating system or an application program. The processor 210 can be implemented with a System on Chip (SoC), for example. The processor 210 can further include a Graphic Processing Unit (GPU) and/or an image signal processor. The processor 210 can include at least part (e.g., a cellular module 221) of the components shown in FIG. 2. The processor 210 can load commands or data received from at least of other components (e.g., a nonvolatile memory) into a volatile memory, process them, and store various data in the nonvolatile memory.

The communication module 220 can have the same or similar configuration to the communication interface 170. The communication module 220 can include, for example, a cellular module 221, a WiFi module 223, a Bluetooth (BT) module 225, a GNSS module 227, an NFC module 228, and an RF module 229. The cellular module 221, for example, can provide voice call, video call, Short Message Service (SMS), or internet service through a communication network. The cellular module 221 can identify and authenticate the electronic device 201 in a communication network by using a subscriber identification module (e.g., the SIM card 224). The cellular module 221 can perform at least part of a function that the processor 210 provides. The cellular module 221 can further include a CP. At least part (e.g., two or more) of the WiFi module 223, the BT module 225, the GNSS module 227, and the NFC module 228 can be included in one integrated chip (IC) or an IC package. The RF module 229, for example, can transmit/receive a communication signal (e.g., an RF signal). The RF module 229, for example, can include a transceiver, a Power Amp Module (PAM), a frequency filter, a Low Noise Amplifier (LNA), or an antenna. According to another embodiment, at least one of the cellular module 221, the WiFi module 223, the BT module 225, the GNSS module 227, and the NFC module 228 can transmit/receive an RF signal through an additional RF module. The SIM card 224, for example, can include a card including a subscriber identification module or an embedded SIM, and also can contain unique identification information (e.g., an Integrated Circuit Card Identifier (IC-CID)) or subscriber information (e.g., an International Mobile Subscriber identity (IMSI)).

The memory 230 (e.g., the memory 130) can include an internal memory 232 or an external memory 234. The internal memory 232 can include at least one of, for example, a volatile memory (e.g., Dynamic RAM (DRAM), Static RAM (SRAM), or Synchronous Dynamic RAM (SDRAM)), and a non-volatile memory (e.g., One Time Programmable ROM (OTPROM), Programmable ROM (PROM), Erasable and Programmable ROM (EPROM), Electrically Erasable and Programmable ROM (EEPROM), mask ROM, flash ROM, flash memory, hard drive, and solid state drive (SSD)). The external memory 234 can include flash drive, for example, Compact Flash (CF), Secure Digital (SD), micro SD, mini SD, extreme digital (xD), Multi-Media Card (MMC), or memory stick. The external memory 234 can be functionally or physically connected to the electronic device 201 through various interfaces.

The sensor module 240 can, for example, measure physical quantities or detect an operating state of the electronic device 201, and thus convert the measured or detected information into electrical signals. The sensor module 240 can include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red, green, blue (RGB) sensor), a bio sensor 240I, a temperature/humidity sensor 240J, an illumination sensor 240K, and an Ultra Violet (UV) sensor 240M. Additionally/alternately, the sensor module 240 can include an E-nose sensor, an electromyography (EMG) sensor, an electroencephalogram (EEG) sensor, an electrocardiogram (ECG) sensor, an infra red (IR) sensor, an iris sensor, and/or a fingerprint sensor. The sensor module 240 can further include a control circuit for controlling at least one sensor therein. The electronic device, as part of the processor 210 or individually, can further include a processor configured to control the sensor module 240 and thus control the sensor module 240 while the processor 210 is sleeping.

The input device 250 can include, for example, a touch panel 252, a (digital) pen sensor 254, a key 256, or an ultrasonic input device 258. The touch panel 252 can use at least one of, for example, capacitive, resistive, infrared, and ultrasonic methods. Additionally, the touch panel 252 can further include a control circuit. The touch panel 252 can further include a tactile layer to provide a tactile response to a user. The (digital) pen sensor 254 can include, for example, part of a touch panel or a sheet for recognition. The key 256 can include, for example, a physical button, a touch key, an optical key, or a keypad. The ultrasonic input device 258 can detect ultrasonic waves from an input means through a microphone (e.g., a microphone 288) and check data corresponding to the detected ultrasonic waves.

The display 260 (e.g., the display 160) can include a panel 262, a hologram device 264, a projector 266, and/or a control circuit for controlling them. The panel 262 can be implemented to be flexible, transparent, or wearable, for example. The panel 262 and the touch panel 252 can be configured with one or more modules. The hologram device 264 can show three-dimensional images in the air by using the interference of light. The projector 266 can display an image by projecting light on a screen. The screen, for example, can be placed inside or outside the electronic device 201. The interface 270 can include a High-Definition Multimedia interface (HDMI) 272, a Universal Serial Bus (USB) 274, an optical interface 276, or a D-subminiature (sub) 278, for example. The interface 270 can be included in the communication interface 170 of FIG. 1, for example. Additionally or alternatively, the interface 270 can include a Mobile High-Definition Link (MHL) interface, a SD card/MMC interface, or an Infrared Data Association (IrDA) standard interface.

The audio module 280, for example, can convert sound into electrical signals and convert electrical signals into sounds. At least some components of the audio module 280 can be included in the input/output interface 150 of FIG. 1, for example. The audio module 280 can process sound information inputted or outputted through a speaker 282, a receiver 284, an earphone 286, or the microphone 288. The camera module 291, as a device for capturing a still image and a video, can include one or more image sensors (e.g., a front sensor or a rear sensor), a lens, an Image Signal Processor (ISP), or a flash (e.g., an LED or a xenon lamp). The power management module 295, for example, can manage the power of the electronic device 201. According to an embodiment, the power management module 295 can include a Power Management IC (PMIC), a charger IC, or a battery or fuel gauge, for example. The PMIC can have a wired and/or wireless charging method. The wireless charging method can include, for example, a magnetic resonance method, a magnetic induction method, or an electromagnetic method, and can further include an additional circuit for wireless charging, for example, a coil loop, a resonant circuit, or a rectifier circuit. The battery gauge can measure the remaining amount of the battery 296, or a voltage, current, or temperature of the battery 296 during charging. The battery 296 can include, for example, a rechargeable battery and/or a solar battery.

The indicator 297 can display a specific state of the electronic device 201 or part thereof (e.g., the processor 210), for example, a booting state, a message state, or a charging state. The motor 298 can convert electrical signals into mechanical vibration and generate a vibration or haptic effect. The electronic device 201 can include a mobile TV supporting device (e.g., a GPU) for processing media data according to standards such as Digital Multimedia Broadcasting (DMB), Digital Video Broadcasting (DVB), or MediaFLO™. Each of the above-mentioned components of the electronic device can be configured with at least one component and the name of a corresponding component can vary according to the kind of an electronic device. In various embodiments, an electronic device (e.g., the electronic device 201) can be configured including at least one of the above-mentioned components or another component, or not including some of the above-mentioned components. Additionally, some of components in an electronic device according to various embodiments of the present disclosure are configured as one entity, so that functions of previous corresponding components are performed identically.

Figure 3:
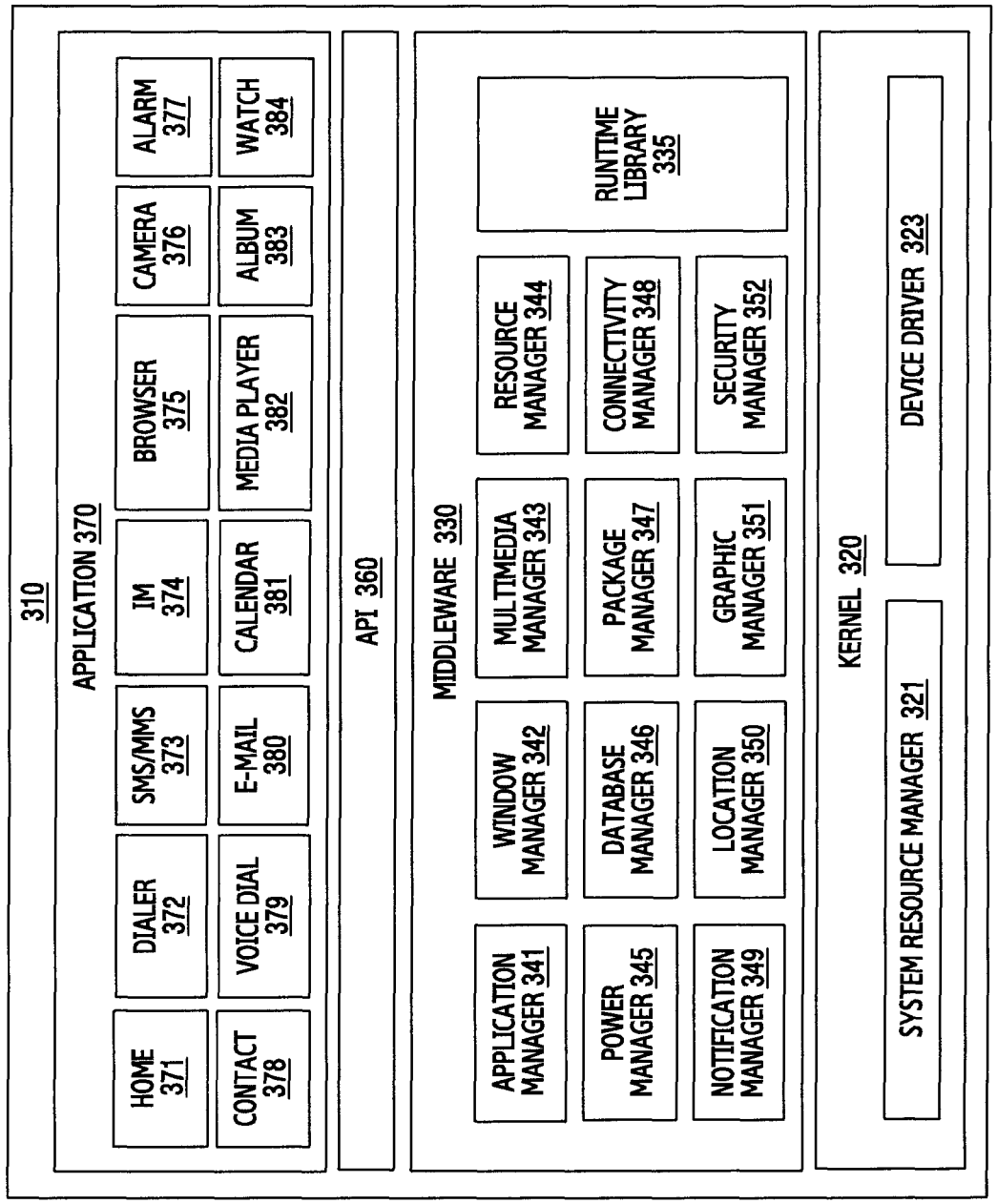
FIG. 3 is a block diagram illustrating a program module according to an embodiment of the present disclosure.

FIG. 3 is a block diagram of a program module according to various embodiments of the present disclosure. The program module 310 (e.g., the program 140) can include an OS for controlling a resource relating to an electronic device (e.g., the electronic device 101) and/or various applications (e.g., the application program 147) running on the OS. The OS can include, for example, Android™, iOS™, Windows™, Symbian™, Tizen™, or Bada™. Referring to FIG. 3, the program module 310 can include a kernel 320 (e.g., the kernel 141), a middleware 330 (e.g., the middleware 143), an API 360 (e.g., the API 145), and/or an application 370 (e.g., the application program 147). At least part of the program module 310 can be preloaded on an electronic device or can be downloaded from an external electronic device (e.g., the electronic devices 102 and 104, a server 106).

The kernel 320 can include, for example, a system resource manager 321 and/or a device driver 323. The system resource manager 321 can control, allocate, or retrieve a system resource. According to an embodiment, the system resource manager 321 can include a process management unit, a memory management unit, or a file system management unit. The device driver 323 can include, for example, a display driver, a camera driver, a Bluetooth driver, a sharing memory driver, a USB driver, a keypad driver, a WiFi driver, an audio driver, or an Inter-Process Communication (IPC) driver. The middleware 330, for example, can provide a function the application 370 utilizes commonly, or provide various functions to the application 370 through the API 360 in order to allow the application 370 to efficiently use a limited system resource inside the electronic device. The middleware 330 can include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 can include, for example, a library module used by a complier to add a new function through a programming language while the application 370 is running. The runtime library 335 can manage input/output, manage memory, or process an arithmetic function. The application manager 341, for example, can manage the life cycle of the applications 370. The window manager 342 can manage a GUI resource used in a screen. The multimedia manager 343 can recognize a format for playing various media files and encode or decode a media file by using the codec in a corresponding format. The resource manager 344 can manage a source code of the application 3740 or a memory space. The power manager 345 can manage the battery or power of the battery and provide power information for an operation of the electronic device. The power manager 345 can operate together with a Basic Input/Output System (BIOS). The database manager 346 can create, search, or modify a database used in the application 370. The package manager 347 can manage installation or updating of an application distributed in a package file format.

The connectivity manager 348 can manage, for example, a wireless connection. The notification manager 349 can provide an event such as incoming messages, appointments, and proximity alerts to the user. The location manager 350 can manage location information of an electronic device. The graphic manager 351 can manage a graphic effect to be provided to the user or a user interface relating thereto. The security manager 352 can provide, for example, system security or user authentication. The middleware 330 can include a telephony manager for managing a voice or video call function of the electronic device, or a middleware module for combining various functions of the above-mentioned components. The middleware 330 can provide a module specialized for each type of OS. The middleware 330 can dynamically delete part of the existing components or add new components. The API 360, as a set of API programming functions, can be provided as another configuration according to OS. For example, in Android or iOS, one API set can be provided for each platform. In Tizen, at least two API sets can be provided for each platform.

According to an embodiment of the present disclosure, the middleware 330 may include a middleware module that may form a combination of the functions of the above-described components or the function of a telephony manager for managing a voice or video call function of an electronic device. According to an embodiment of the present disclosure, the middleware 330 may provide a module specified for each type of operating system. The middleware 330 may dynamically remove some of the existing components or add new components. The API 360 is, for example, a set of API programming functions, and may be provided in a different configuration based on an OS. For example, in the case of Android or iOS, one API set may be provided for each platform. In the case of Tizen, two or more API sets may be provided for each platform.

The application 370 can include, for example, a home 371, a dialer 372, an SMS/MMS 373, an Instant Message (IM) 374, a browser 375, a camera 376, an alarm 377, a contact 378, a voice dial 379, an e-mail 380, a calendar 381, a media player 382, an album 383, a clock 384, health care (e.g., measure an exercise amount or blood sugar), or environmental information (e.g., air pressure, humidity, or temperature information) provision application. The application 370 can include an information exchange application for supporting information exchange between the electronic device and an external electronic. The information exchange application can include, for example, a notification relay application for relaying specific information to the external device or a device management application for managing the external electronic device. For example, the notification relay application can relay notification information from another application of the electronic device to an external electronic device, or receive and forward notification information from an external electronic device to the user. The device management application, for example, can install, delete, or update a function (e.g., turn-on/turn off of the external electronic device itself (or some components) or display brightness (or resolution) adjustment) of an external electronic device communicating with the electronic device, or an application operating in the external electronic device. The application 370 can include a specified application (e.g., a health care application of a mobile medical device) according to a property of the external electronic device. The application 370 can include an application received from an external electronic device. At least part of the program module 310 can be implemented (e.g., executed) with software, firmware, hardware the processor 210), or a combination of at least two of them, and include a module, a program, a routine, a set of instructions, or a process for executing one or more functions.

The term "module" used in various embodiments of the present disclosure can imply a unit including hardware, software, and firmware or any suitable combination. The "module" can be interchangeably used with a term such as a unit, logic, a logical block, a component, a circuit, and the like. The "module" can be a minimum unit of an integral component or can be a part thereof. The "module" can be a minimum unit for performing one or more functions or may be a part thereof. The "module" can be mechanically or electrically implemented. For example, the "module" according to various embodiments of the present disclosure can include at least one of an Application-Specific Integrated Circuit (ASIC) chip, a Field-Programmable Gate Arrays (FPGAs), and a programmable-logic device, which are known or will be developed and which perform certain operations. At least some parts of a device (e.g., modules or functions thereof) or a method (e.g., operations) based on the various embodiments of the present disclosure can be implemented with an instruction stored in a non-transitory computer-readable storage medium (e.g., the memory 130) as a program module. When the instruction is executed by one or more processors (e.g., the processor 120), the one or more processors can perform a function corresponding to the instruction. The non-transitory computer readable recording medium can include, for example, a hard disk, a floppy disc, a magnetic medium (e.g., a magnetic tape), an optical storage medium (e.g., a Compact Disc-ROM (CD-ROM) or a DVD, a magnetic-optic medium (e.g., a floptical disc)), and an internal memory. The instruction can include code created by a compiler or code executable by an interpreter. The module or program module can further include at least one or more components among the aforementioned components, or can omit some of them, or can further include additional other components. Operations performed by a module, program module, or other components of the various embodiments of the present disclosure can be executed in a sequential, parallel, repetitive, or heuristic manner. In addition, some of the operations can be executed in a different order or may be omitted, or other operations may be added.

Figure 4:
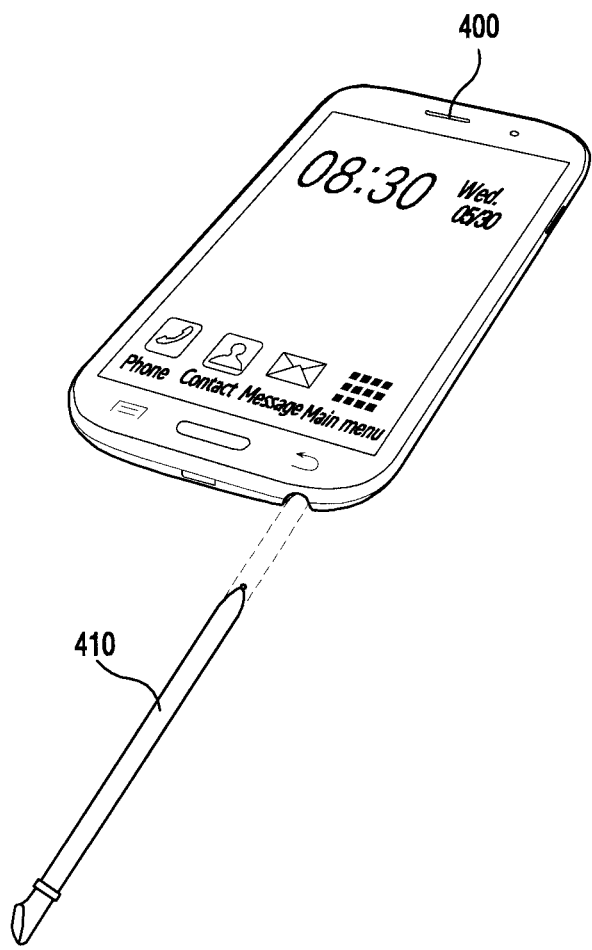
FIG. 4 is a perspective view of an electronic device to which a stylus pen is detachable according to an embodiment of the present disclosure.

FIG. 4 is a perspective view of an electronic device to which a stylus pen is detachable according to an embodiment of the present disclosure.

Referring to FIG. 4, an electronic device 400 (e.g., the electronic device 101 or the electronic device 201) according to the present disclosure may include a stylus pen 410 (e.g., the electronic device 101 or the electronic device 201). According to an embodiment of the present disclosure, the stylus pen 410 may be securable (e.g., installed or inserted) and detachment (e.g., removable, extractable) from a predetermined position on a lateral side of the electronic device 400. The electronic device 400 may execute wired communication or wireless communication (e.g., short-range wireless communication), such as Bluetooth, Near Field Communication (NFC), or Infrared Ray (IR), WiFi, or the like, with the stylus pen 410.

According to an embodiment of the present disclosure, when the stylus pen 410 is installed, the electronic device 400 may execute charging of the stylus pen 410 by providing power to the stylus pen 410. According to an embodiment of the present disclosure, when the electronic device 400 detects or senses that the stylus 410 has been detached, the electronic device 400 may determine information associated with an application that is currently executed or that is selected for execution. The electronic device 400 may transmit the determined information associated with the application to the stylus pen 410. To this end, the electronic device 400 and the stylus pen 410 may communication with each other via, for example, wireless communication or wired communication.

According to an embodiment of the present disclosure, the stylus pen 410, having received the information associated with the application, may thus activate a sensor corresponding to the received information. The stylus pen 410 may obtain data (hereinafter: "sensing information") through the activated sensor. According to an embodiment of the present disclosure, the stylus pen 410 may transmit the obtained sensing information to the electronic device 400. The sensing information may be transmitted to the electronic device 400 through, for example, the wireless communication (or, in some embodiments, wired communication). Also, for example, when the stylus pen 410 is in contact with the electronic device 400 (e.g., a tip of the stylus pen 410 may contact a display unit of the electronic device 400), the stylus pen 410 may transmit sensing information to the electronic device 400 based on, for example, an Electronic Magnetic resonance (EMR) scheme.

According to an embodiment of the present disclosure, the electronic device 400 may display the sensing information received from the stylus pen 410. For example, when the tip of the stylus pen 410 is in contact with the display unit, the electronic device 400 may control a display to display the sensing information, disposed near or on a location where the tip is in contact with the display unit. For example, the electronic device 400 may provide an application service to a user using the received sensing information. The application service provided to the user may include a service related to a user's health condition, a service associated with learning, a service associated with controlling the electronic device 400 or an external device (not illustrated), and a service associated with user authentication.

According to an embodiment of the present disclosure, when it is determined that the stylus pen 410 is fully charged, the electronic device 400 may display the same. When the stylus pen 410 is installed, the electronic device 400 may display the residual quantity of battery power of the stylus pen 410 in the electronic device 400. According to an embodiment of the present disclosure, the electronic device 400 may determine whether to charge the stylus pen 410 based on the residual quantity of battery power of the electronic device 400 or the stylus pen 410. The electronic device 400 may determine whether to charge the stylus pen 410 based on a battery power consumption rate of the electronic device 400 or the stylus pen 410. The electronic device 400 may determine whether to charge the electronic device 400 based on the amount of battery power consumption or a battery power consumption history of an application that is currently executed.

According to an embodiment of the present disclosure, the electronic device 400 may determine the residual quantity of the battery power of the electronic device 400 or the strength of the charging current of the stylus pen 410, When the stylus pen 410 is fully charged, the electronic device 400 may terminate charging the stylus pen 410, or may repeat discharging and charging. The electronic device 400 may suspend charging the stylus pen 410 when the temperature of the stylus pen 410 is higher than a predetermined temperature. The electronic device 400 may suspend charging the stylus pen 410 when the residual quantity of the battery power of the electronic device 400 is less than a predetermined amount.

Figure 5:
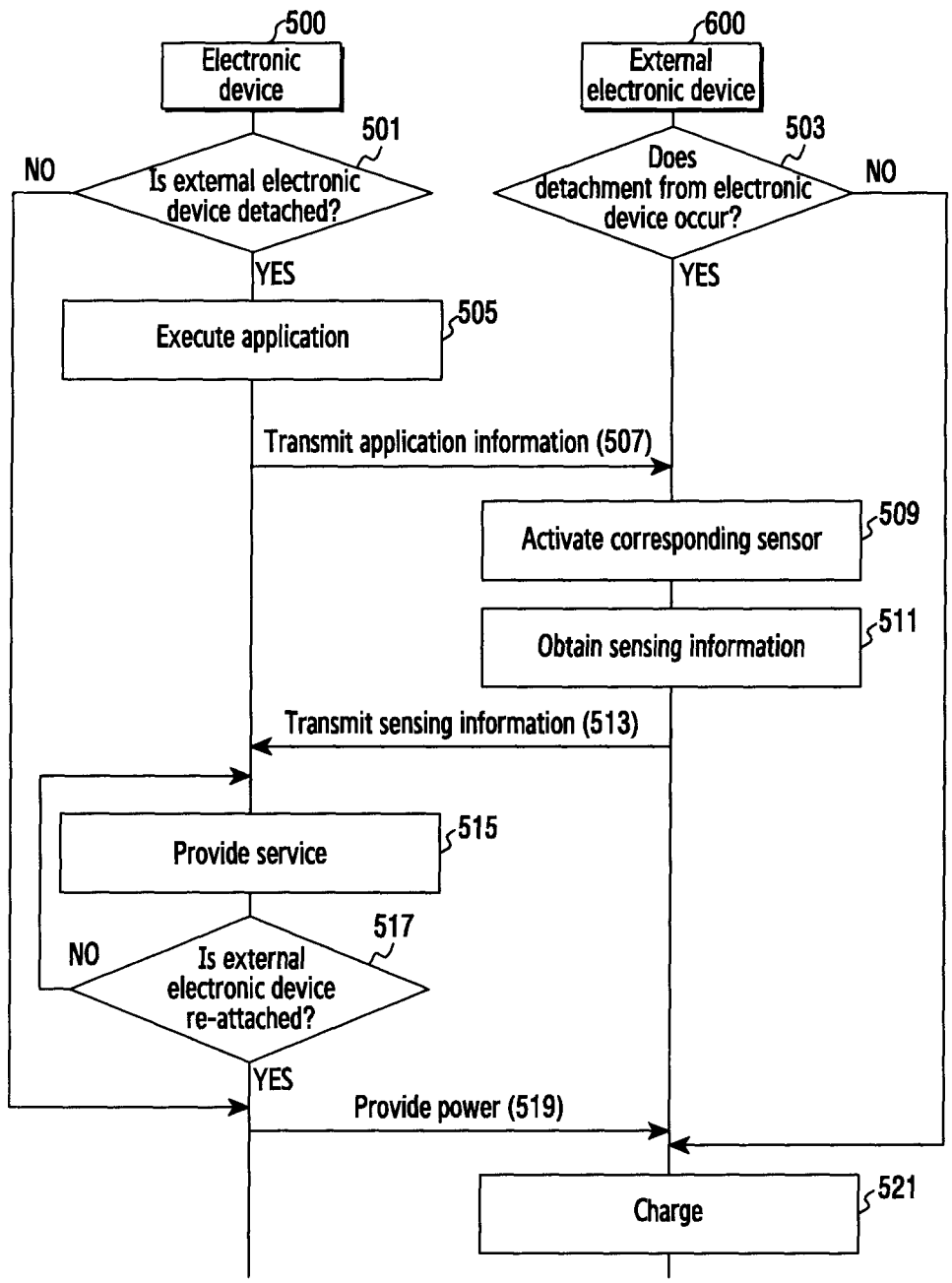
FIG. 5 is a flowchart illustrating an operation method of an electronic device and an external electronic device according to an embodiment of the present disclosure.

FIG. 5 is a flowchart illustrating an operation method of an electronic device and an external electronic device 500 (e.g., a stylus pen) according to an embodiment of the present disclosure. According to an embodiment of the present disclosure, some of operations 501, 505, 507, 515, 517, and 519 may be executed through an electronic device 500 (e.g., the electronic device 400, 101, or 201) or a processor of the electronic device 500 (e.g., the processor 120 or 210 or a sensor manager). According to an embodiment of the present disclosure, at least some of operations 503, 509, 511, 513, and 521 may be executed through an external electronic device 600 (e.g., the electronic device 102, 104, or 201 or the stylus pen 410) or a processor of the external electronic device 600 (e.g., the processor 120 or 210, the program module 310, or a sensor manager).

Referring to FIG. 5, in operation 501, the electronic device 500 may detected whether the external electronic device 600 has been detached (e.g., removed, decoupled, extracted from the electronic device 500). According to an embodiment of the present disclosure, when the detachment of the external electronic device 600 is not detected in operation 501, the electronic device 500 may perform operation 519 and thus provide power to the external electronic device 600 that is installed (e.g., coupled, inserted, stowed or secured to the electronic device 500, as seen for example in FIG. 4).

In operation 503, the external electronic device 600 may detected whether the external electronic device 600 is detached from the electronic device 500. According to an embodiment of the present disclosure, when the detachment from the electronic device 500 is not detected in operation 503, the external electronic device 600 may perform operation 521 and execute charging through power provided from the electronic device 500.

According to an embodiment of the present disclosure, when the detachment of the external electronic device 600 is detected in operation 501, the electronic device 500 may perform operation 505. In operation 505, the electronic device 500 may execute an application, and may determine certain information associated with the application. The information associated with the application, for example, may be a type of sensing information utilized by the application for providing an application service to a user, the name of an application, the unique identifier of the application, whether the execution of the application starts, a command for activating a sensor corresponding to the application, or the like. Subsequent to operation 505, the electronic device 500 may transmit the determined information associated with the application to the external electronic device 600 in operation 507.

According to an embodiment of the present disclosure, the electronic device 500 transmits the determined information associated with the application to the external electronic device 600 in operation 507. The electronic device 500, for example, may transmit the information associated with the application to the external electronic device 600 through short-range wireless communication. According to an embodiment of the present disclosure, the external electronic device 600 may then activate a sensor corresponding to the indicated application information in operation 509. For example, the external electronic device 600 may determine the application information received from the electronic device 500, and may activate the sensor corresponding to the application information. The sensor corresponding to the application information, for example, may be a sensor for obtaining sensing information that is utilized to execute the application. For example, when the application information corresponds to an application that provides heartbeat information, the electronic device 500 may utilize heartbeat information to execute the application. To this end, the external electronic device 600 may activate a heartbeat sensor installed therein that is capable of obtaining heartbeat information in order to provide the requested information. Also, when the application information corresponds to an application that provides blood pressure information, the electronic device 500 may utilize blood pressure information to execute the application. To this end, the external electronic device 600 may activate a blood pressure sensor that is capable of obtaining blood pressure information. In operation 511, the external electronic device 600 may obtain the sensing information (e.g., heartbeat information or blood pressure information) from the activated sensor.

In operation 513, the external electronic device 600 may transmit the obtained sensing information to the electronic device 500. The external electronic device 600, for example, may transmit sensing information to the electronic device 500 through short-range wireless communication (or wired communication). For example, when the tip of the external electronic device 600 is in contact with a display unit of the electronic device 500, the external electronic device 600 may transmit sensing information to the electronic device 500 through an EMR.

In operation 515, the electronic device 500 provides a service associated with the application based on the sensing information received from the external electronic device 600. When the installation of the external electronic device 600 that is detached in operation 501 is sensed in operation 517, the electronic device 500 executes operation 519. In operation 519, the electronic device 500 may provide power to the external electronic device 600, in operation 521, the external electronic device 600 executes charging using power provided from the electronic device 500.

According to an embodiment of the present disclosure, at least one operation out of operations 501 to 521 may be omitted, or the order of operations may be changed. According to an embodiment of the present disclosure, operation 501 may be omitted. Accordingly, in operation 505, the electronic device 500 executes an application irrespective of the detachment of the external electronic device 600. According to an embodiment of the present disclosure, after some of operation 505 is executed, operation 501 may be executed. For example, in operation 505, the electronic device 500 may execute an application. In operation 501, the electronic device 500 may sense the detachment of the external electronic device 600. Based on the detachment of the external electronic device 600 from the electronic device 500, the electronic device 500 determines the information associated with the application in operation 505.

According to an embodiment of the present disclosure, operations 517 to 521 may be omitted. Accordingly, the external electronic device 600 may be supplied with power irrespective of the installation to the electronic device 500. For example, the external electronic device 600 may be supplied with power wirelessly through the electronic device 500 or another external electronic device (not illustrated) in the state in which the external electronic device 600 is not installed to the electronic device 500. Also, the external electronic device 600 may not be supplied with power in the state in which the external electronic device 600 is installed to the electronic device 500.

Figure 6:
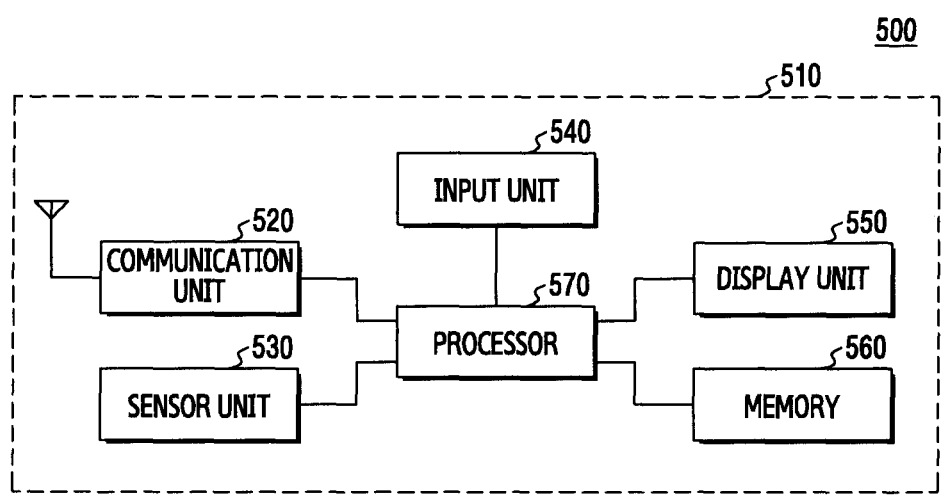
FIG. 6 is a block diagram of an electronic device according to an embodiment of the present disclosure.

FIG. 6 is a block diagram illustrating the main components of an electronic device according to an embodiment of the present disclosure.

Referring to FIG. 6, the electronic device 500 (e.g., the electronic device 101 or 201), according to an embodiment of the present disclosure, may include: a communication unit 520 (e.g., the communication interface 170, the communication module 220, and the interface 270); a sensor unit 530 (e.g., the sensor module 240); an input unit 540 (e.g., the input/output interface 150, the input device 250, the audio module 280, the speaker 282, the receiver 284, the earphones 286, the microphone 288, the camera module 291, the indicator 297, or the motor 298); a display unit 550 (e.g., the display 160 or the display 260), a memory 560 (e.g., the memory 130 or the memory 230); and a processor 570 (e.g., the processor 120, the processor 210, the program module 310, or a sensor manager). Each component may be disposed inside or outside a housing 510.

The communication unit 520 may perform communication in the electronic device 500. According to an embodiment of the present disclosure, the communication unit 520 may communicate with an external device (not illustrated), such as a server, another electronic device, or the like, in various schemes. For example, the communication unit 520 may perform at least one of wireless communication and wireless communication. The communication unit 520 may access at least one of a mobile communication network and a data communication network. For example, the external device may include an electronic device, a base station, a server, and a satellite. The communication scheme may include Long Term Evolution (LTE), Wideband Code Division Multiple Access (WCDMA), Global System for Mobile Communications (GSM), Wireless Fidelity (WiFi), Bluetooth, Near Field Communications (NFC) or Infrared Ray (IR). The communication unit 520 may perform short-range wireless communication with an external electronic device (e.g., the accessory device 600) that is installed to/detached from the electronic device 500, through short-range wireless communication including Bluetooth, NFC, or IR. According to an embodiment of the present disclosure, the communication unit 520 may perform Electronic Magnetic Resonance (EMR) communication.

According to an embodiment of the present disclosure, the sensor unit 530 may sense whether an external electronic device is installed/detached, and may transfer the same to the processor 570.

The input unit 540 may generate input data in the electronic device 500. The input unit 540 may generate input data in response to a user input of the electronic device 500. The input unit 540 may include at least one input means. The input unit 540 may include, for example, a key pad, a dome switch, a physical button, a touch panel, and a jog & shuttle. The touch panel may sense coordinate information and the like associated with a movement on a touch panel (for example, a touch provided by a user's finger and an external electronic device (e.g., the stylus pen 410)), and may transfer the same to the processor 570.

According to an embodiment of the present disclosure, the display unit 550 may include a Liquid Crystal Display (LCD), a Light Emitting Diode (LED) display, an Organic LED (OLED) display, a Micro Electro Mechanical System (MEMS) display, or an electronic paper display. The display unit 550 may include, for example, a plurality of light emitting devices. For example, the display unit 550 may be embodied as a touch screen by coupling with the input unit 540. According to an embodiment of the present disclosure, the display unit 550 embodied as a touch screen may transfer, to the processor 570, coordinate information and the like associated with a movement sensed from the surface of the display unit 550, for example, a touch provided by an external electronic device (e.g., the stylus pen 410), and the like.

According to an embodiment of the present disclosure, the memory 560 may store operating programs of the electronic device 500. The memory 560 may store a plurality of applications that may be executed based on a user input.

According to an embodiment of the present disclosure, when an external electronic device (e.g., the stylus pen 410) is installed, the processor 570 provides power to the external electronic device (e.g., the stylus pen 410), and controls the charging of the external electronic device (e.g., the stylus pen 410). According to an embodiment of the present disclosure, when the detachment of the external electronic device (e.g., the stylus pen 410) is sensed, the processor 570 may determine information associated with an application that is currently executed or that is selected for execution. According to an embodiment of the present disclosure, the processor 570 may transmit the determined information associated with the application to the external electronic device (e.g., the stylus pen 410). According to an embodiment of the present disclosure, the processor 570 may provide a service associated with the application based on the sensing information received from the external electronic device (e.g., the stylus pen 410). For example, the processor 570 may provide at least one service out of: a service associated with the health of a user, a service associated with controlling the electronic device 500 or an external device, and a service associated with user authentication, based on the application.

The electronic device 500, according to an embodiment of the present disclosure, may include a communication interface (e.g., the communication unit 520) and a processor (e.g., the processor 570). The processor 570 may be configured to perform: determining an application that is executed in the electronic device 500; when the application is a first application, transmitting first information corresponding to the first application to an external electronic device (e.g., an accessory device (e.g., the stylus pen 410) including a first sensor and a second sensor, through the communication interface 520; when the application is a second application, transmitting second information corresponding to the second application to an external electronic device (e.g., the stylus pen 410), through the communication interface 520; and receiving, to the external electronic device (e.g., the stylus pen 410), data obtained through a sensor out of the first sensor and the second sensor, which corresponds to transmitted information out of the first information and the second information.

According to various embodiments of the present disclosure, based on at least some of a situation in which the external electronic device (e.g., the stylus pen 410) is separated from the electronic device 500, the processor 570 may be configured to transmit information to the external electronic device (e.g., the stylus pen 410).

According to various embodiments of the present disclosure, the processor 570 may be configured: to display an object for inputting data through a display (e.g., the display unit 550) included in the electronic device 500; and based on at least some of a situation in which at least a part of the external electronic device (e.g., the stylus pen 410) is in contact with an area of the display which corresponds to the object, to display the received data in the area.

Figure 7:
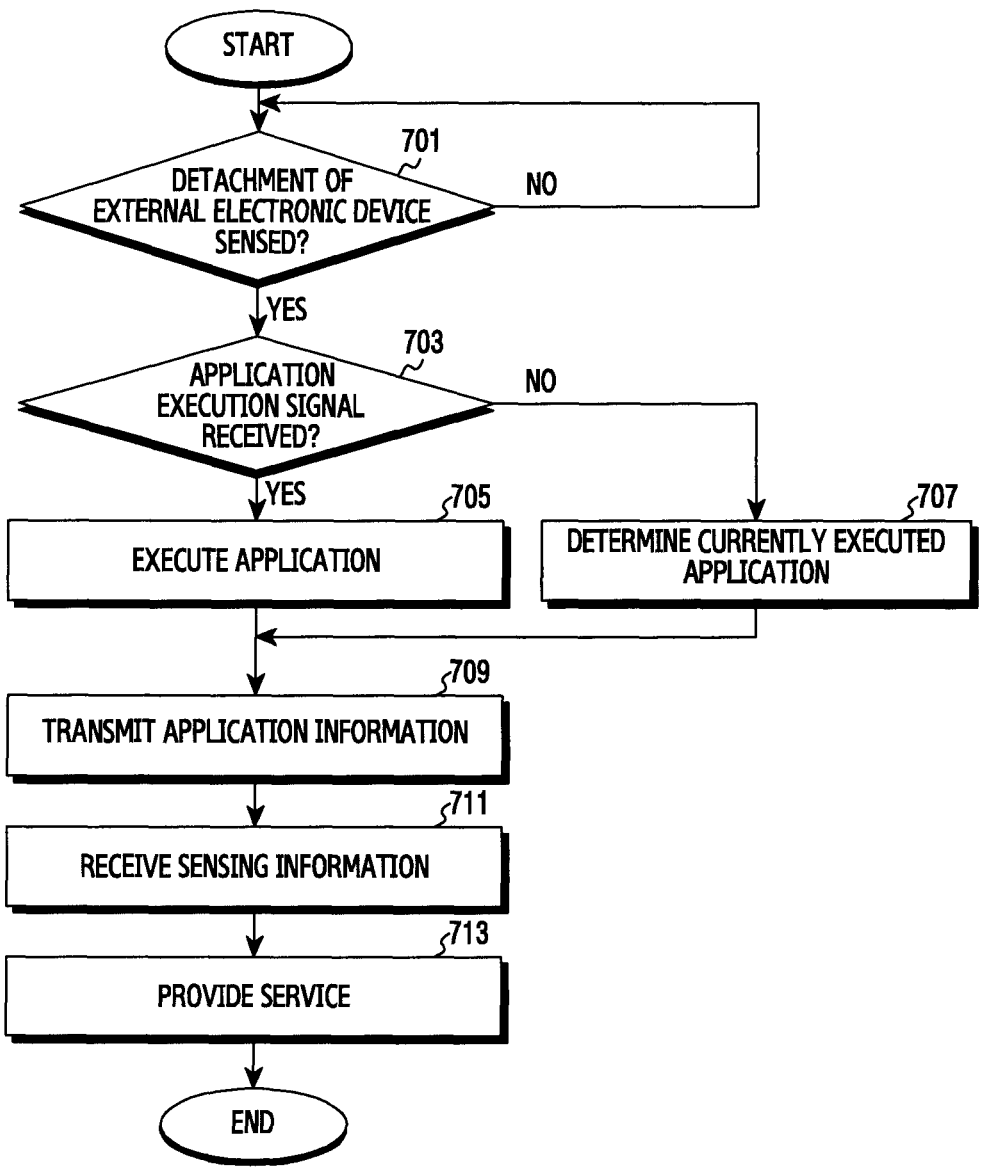
FIG. 7 is a flowchart illustrating operations of an electronic device according to an embodiment of the present disclosure.

FIG. 7 is a flowchart illustrating operations of an electronic device according to an embodiment of the present disclosure. According to an embodiment of the present disclosure, at least some of operations 701 to 713 may be executed through an electronic device (e.g., the electronic device 101, 201, 400 or 500) or a processor of the electronic device (e.g., the processor 120, 210, or 570, the program module 310, or a sensor manager). Referring to FIG. 7, in operation 701, the electronic device (e.g., the processor 570) senses the detachment of an external electronic device (e.g., an accessory device, such as a stylus pen, a headset, a watch, or the like) that is installed to the electronic device (e.g., the electronic device 500). The electronic device (e.g., the processor 570) may then perform operation 703 when the detachment of the external electronic device (e.g., the stylus pen 410) is sensed in operation 701. When the detachment of the external electronic device (e.g., the stylus pen 410) is not sensed in operation 701, the electronic device (e.g., the processor 570) may continue to monitor for the detachment of the external electronic device (e.g., the stylus pen 410) in real time or by polling periodical determinations.

In operation 703, the electronic device (e.g., the processor 570) may sense whether an execution signal with respect to an application is received. When the execution signal with respect to the application is received in operation 703, the electronic device (e.g., the processor 570) may perform operation 705. In operation 705, the electronic device (e.g., the processor 570) executes the application corresponding to the received execution signal. The electronic device (e.g., the processor 570) performs operation 707 When the execution signal with respect to the application is not received in operation 703. In operation 707, the electronic device (e.g., the processor 570) may determine a currently executed application.

In operation 709, the electronic device (e.g., the processor 570) transmits, to the external electronic device (e.g., the stylus pen 410), application information associated with the application that is executed in operation 705, or application information associated with the application determined in operation 707. The electronic device (e.g., the processor 570) may transmit the application information to the external electronic device (e.g., the stylus pen 410) through, for example, short-range wireless communication. When the detachment of the external electronic device (e.g., the stylus pen 410) is sensed (e.g., at a point in time when detachment is sensed), the electronic device (e.g., the processor 570) may activate short-range wireless communication, and then execute communication with the external electronic device (e.g., the stylus pen 410) via the activated short-range wireless communication. The application information may include, for example, sensing information that is utilized to provide a user with an application service.

In operation 711, the electronic device (e.g., the processor 570) receives sensing information from the external electronic device (e.g., the stylus pen 410). The sensing information may be biometric information that corresponds to the application information that is transmitted to the external electronic device (e.g., the stylus pen 410) in operation 709. For example, when the application is an application for providing a service associated with the health of a user, the sensing information may be biometric information associated with health. When the application is an application for providing a service associated with the learning of a user, the sensing information may be biometric information associated with learning. When the application is an application for providing a service associated with user authentication, the sensing information may be biometric information associated with authentication. When the application is an application for controlling an electronic device or an external device (e.g., a control device of an air conditioner, a lighting installation, an audio device, sporting equipment, and the like), the sensing information may be biometric information associated with control.

Figure 11:
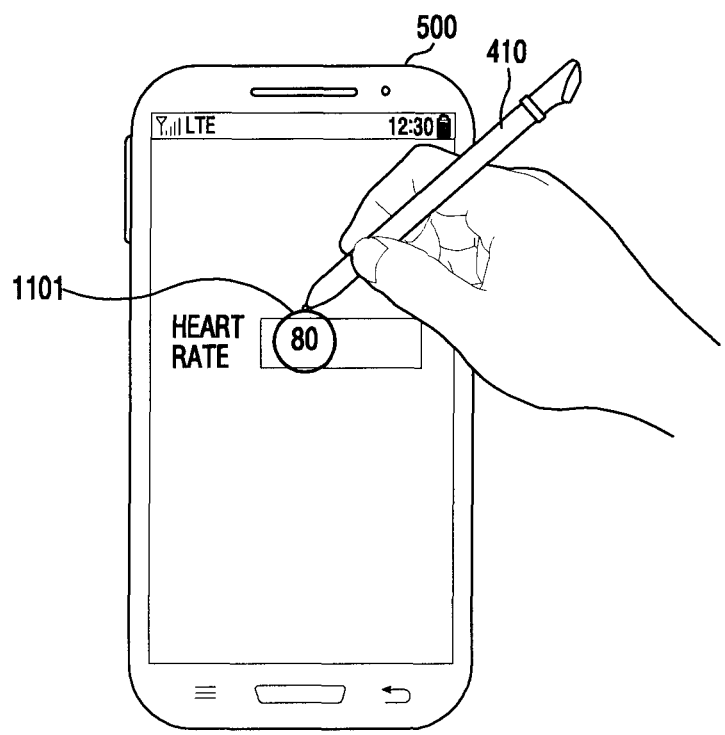
FIG. 11 is a diagram illustrating a screen which shows the operations of an electronic device to provide a service according to various embodiments of the present disclosure.
Figure 12:
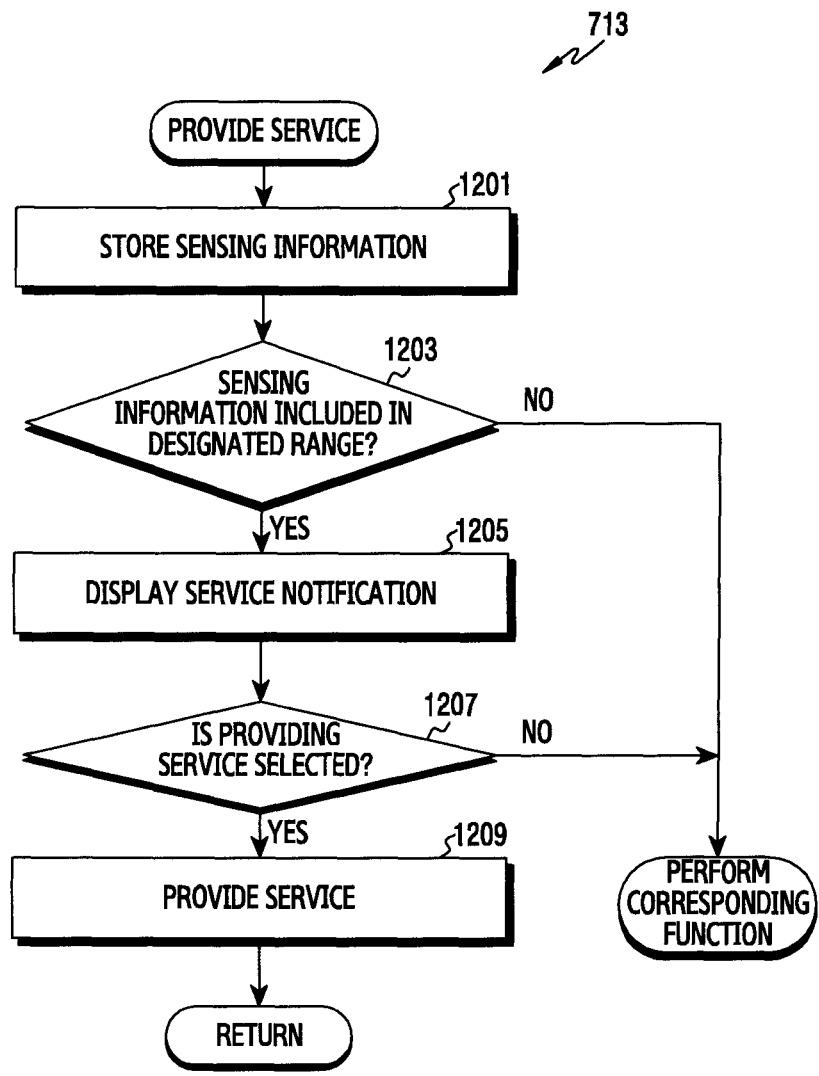
FIG. 12 is a flowchart illustrating operations of an electronic device to provide a service according to various embodiments of the present disclosure.
Figures 13A, 13B:
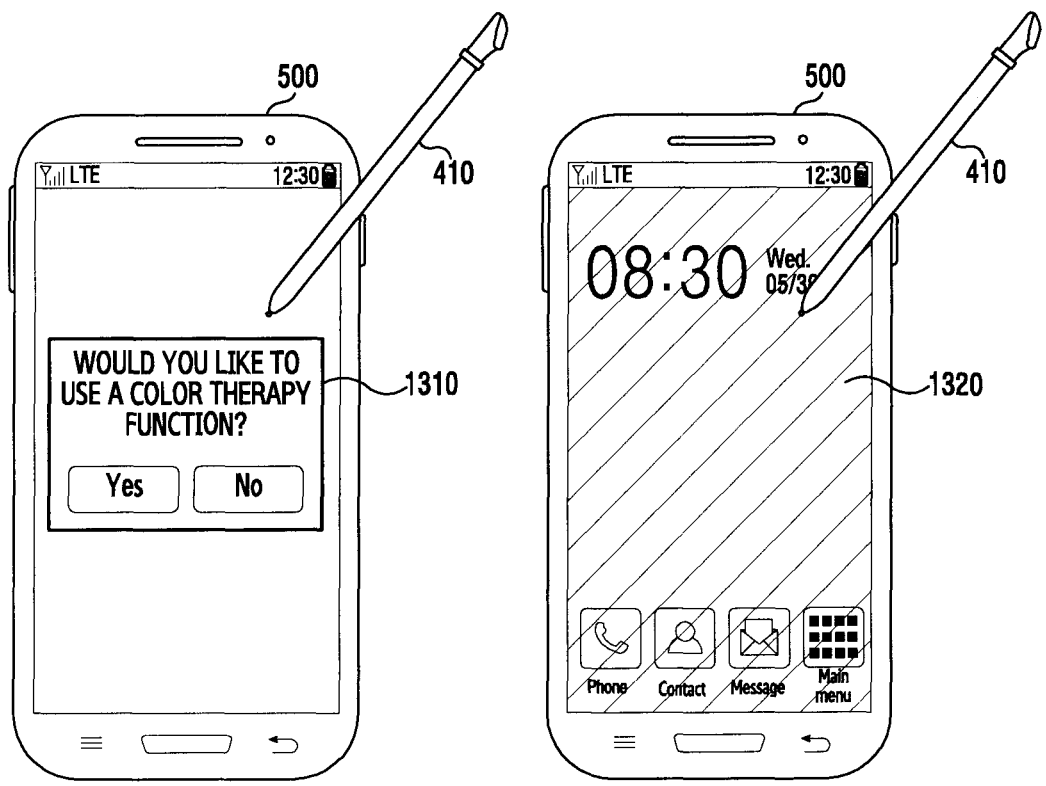
FIG. 13A and FIG. 13B are diagrams illustrating screens which show the operations of an electronic device to provide a service according to various embodiments of the present disclosure.
Figure 14:
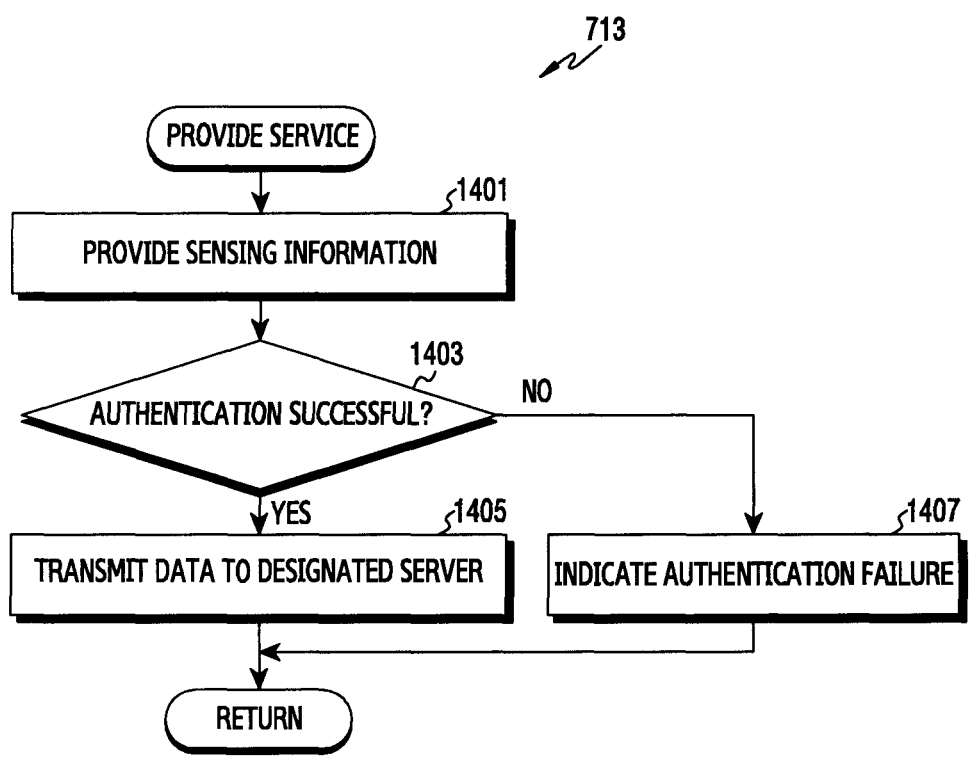
FIG. 14 is a flowchart illustrating operations of an electronic device to provide a service according to various embodiments of the present disclosure.
Figure 15A:
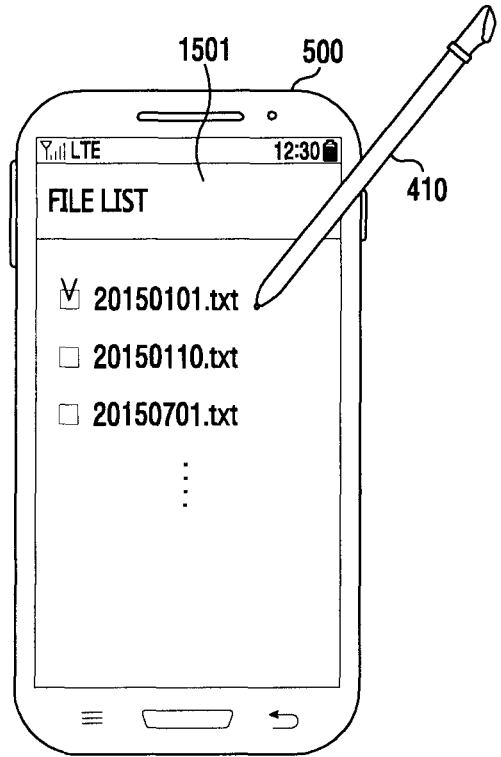
FIG. 15A, FIG. 15B and FIG. 15C are diagrams illustrating screens which show the operations of an electronic device to provide a service according to various embodiments of the present disclosure.
Figure 15B:
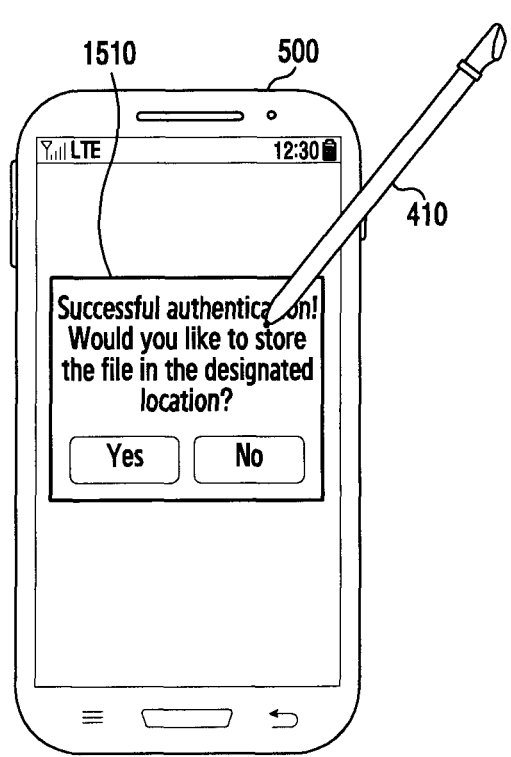
Figure 15C:
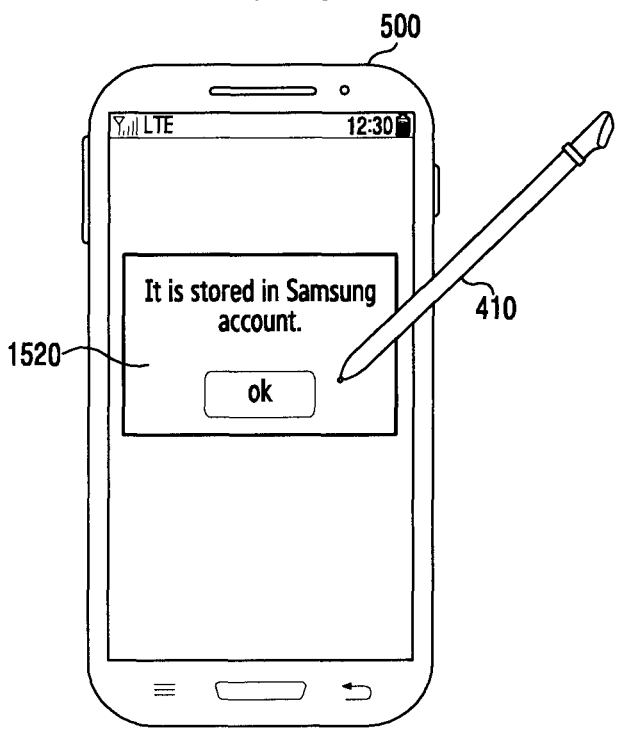
Figure 16:
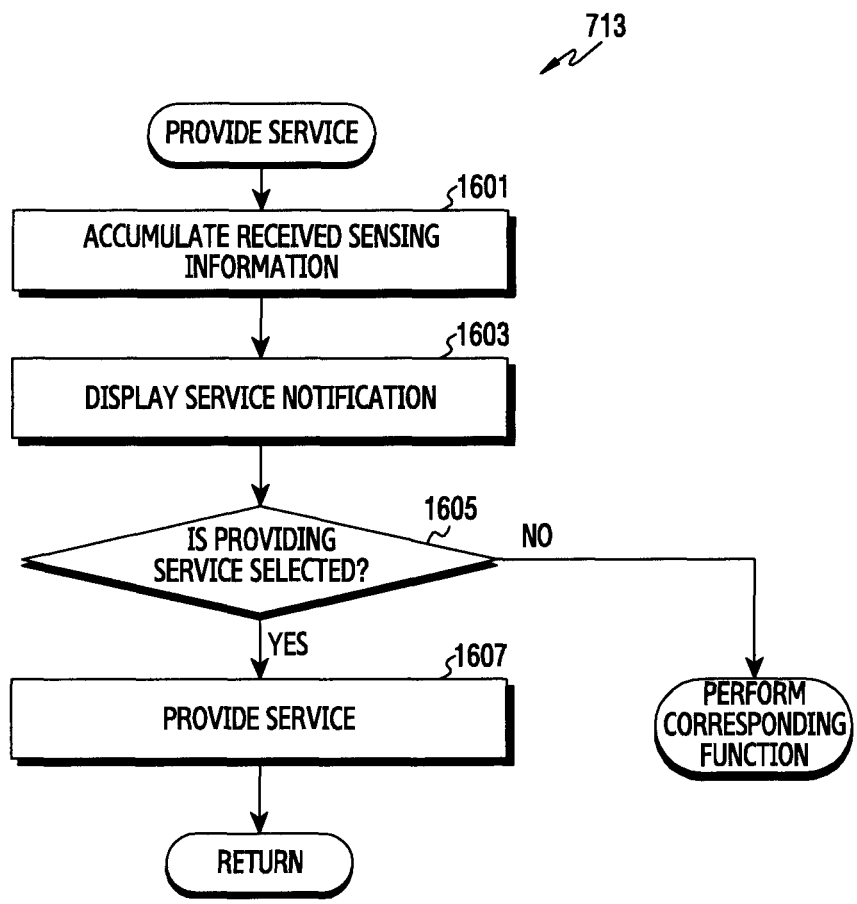
FIG. 16 is a flowchart illustrating operations of an electronic device to provide a service according to various embodiments of the present disclosure.

In operation 713, the electronic device (e.g., the processor 570) provides a service using the received sensing information. Hereinafter, providing a service will be described in detail with reference to FIGS. 8 to 15. FIGS. 8 to 11 provide descriptions relating to providing a service associated with the health of a user. FIGS. 12 and 13 provide descriptions relating to providing a service associated with the controlling of an electronic device. FIGS. 14 and 15 provide descriptions relating to providing a service associated with authenticating a user, FIG. 16 provides descriptions relating to providing a service associated with the learning of a user.

According to an embodiment of the present disclosure, at least one operation out of operations 701 to 713 may be omitted, or the order of operations may be changed. For example, operation 701 may be omitted. Accordingly, the electronic device (e.g., the processor 570) may sense whether an application execution signal is received in operation 703, irrespective of the detachment of the external electronic device the stylus pen 410).

For example, operations 701, 703, 705, and 713 may be omitted. Accordingly, the electronic device (e.g., the processor 570) determines a currently executed application in operation 707. In operation 709, the electronic device (e.g., the processor 570) transmits information corresponding to the application to the external electronic device (e.g., the stylus pen 410). For example, when the application is a first application, the electronic device (e.g., the processor 570) may transmit first information (e.g., a request for data obtained through a first sensor) corresponding to the first application to the external electronic device (e.g., the stylus pen 410) including the first sensor and a second sensor. Also, when the application is a second application, the electronic device (e.g., the processor 570) may transmit second information (e.g., a request for data obtained through the second sensor) corresponding to the second application to the external electronic device (e.g., the stylus pen 410).

In operation 711, the electronic device the processor 570) receives sensing information from the external electronic device (e.g., the stylus pen 410). For example, the electronic device (e.g., the processor 570) may receive, from the external electronic device (e.g., the stylus pen 410) including the first sensor and the second sensor, data obtained through a sensor out of the first sensor and the second sensor, which corresponds to information corresponding to the application.

Figure 8:
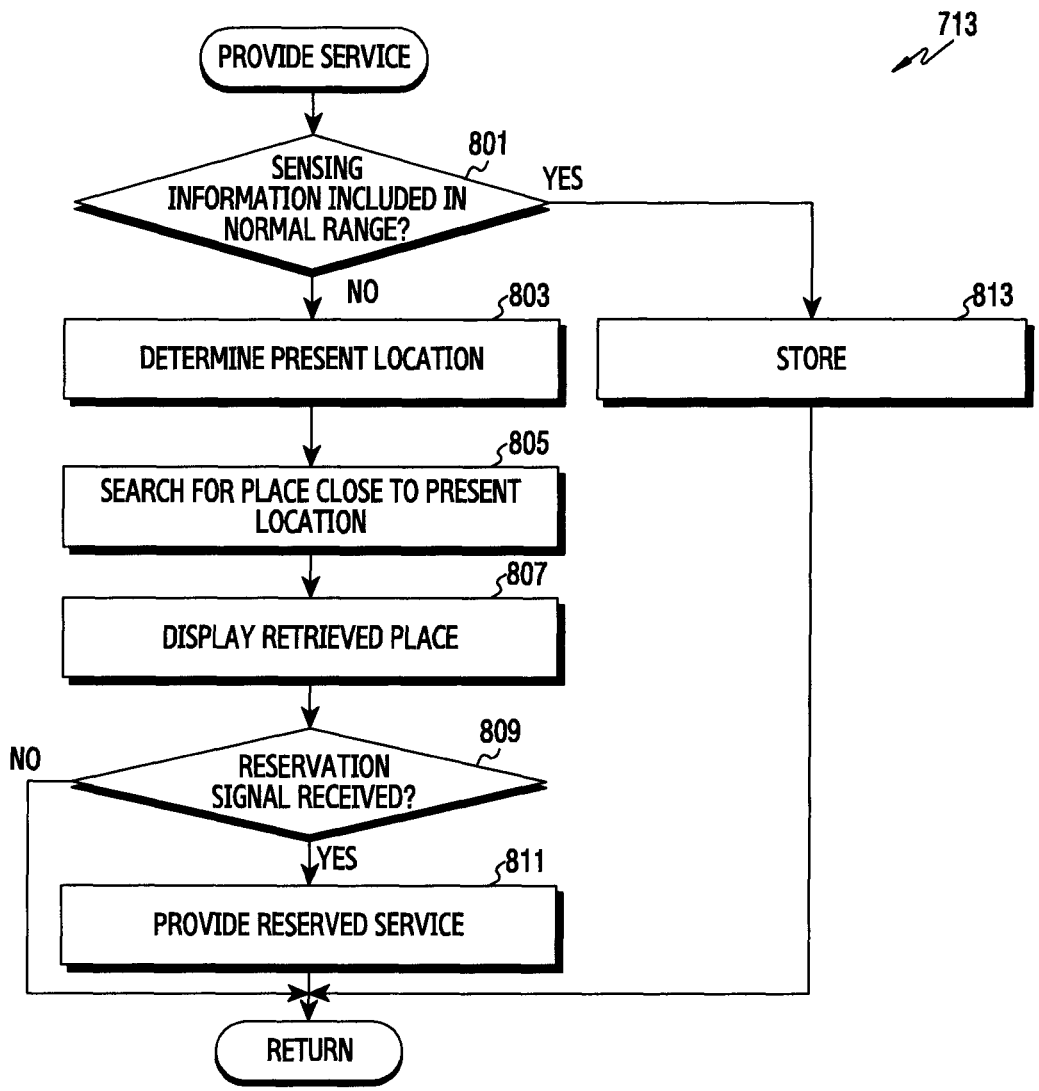
FIG. 8 is a flowchart illustrating operations of an electronic device to provide a service according to an embodiment of the present disclosure.

FIG. 8 is a flowchart illustrating operations of an electronic device to provide a service according to an embodiment of the present disclosure. FIGS. 9A to 9D are diagrams illustrating screens which show the operations of an electronic device to provide a service according to an embodiment of the present disclosure. According to an embodiment of the present disclosure, at least some of operations 801 to 813 may be executed through an electronic device (e.g., the electronic device 101, 201, or 400) or a processor of the electronic device (e.g., the processor 120, 210, or 570, the program module 310, or a sensor manager).

Referring to FIGS. 8 and 9, the electronic device (e.g., the processor 570) determines Whether sensing information received from an external electronic device (e.g., the stylus pen 410, a headset, or a watch) indicates that a corresponding quantity or measurement exists within a designated (e.g., predetermined) range in operation 801. For example, when the sensing information is body temperature, the electronic device may detect whether a body temperature measurement value is within a normal temperature range (e.g., 36.0~37.7° C.). When the result of determination in operation 801 indicates that the sensing information is included in the designated range (e.g., when the body temperature measurement value is in a normal range), the electronic device (e.g., the processor 570) may perform operation 813. In operation 813, the electronic device (e.g., the processor 570) may store, in a memory (e.g., the memory 560), a time at which the body temperature was measured, and the actual body temperature measurement value itself.

When it is determined that the sensing information is not indicated within the designated range (e.g., When the body temperature measurement value is indicated as being outside the normal range) in operation 801, the electronic device (e.g., the processor 570) performs operation 803. In operation 803, the electronic device (e.g., the processor 570) determines its present location, for example, through a Global Positioning System (GPS) or WiFi. In operation 805, the electronic device (e.g., the processor 570) searches for a corresponding location, institution or place (e.g., hospital) that is relevant to the measurement and close to the determined present location. For example, the electronic device (e.g., the processor 570) may search for a place (e.g., hospital) existing within a radius of about 2 Km based on the determined present location. Thus, when the sensing information is indicated as being outside of the designated range (e.g., the body temperature measurement value is out of the normal range), the electronic device (e.g., the processor 570) searches for a designated or correlating institution of place (e.g., a special hospital associated with diseases that are directly connected with an abnormal body temperature, such as cold, tonsillitis, and the like) corresponding to the sensing information.

Figures 9A, 9B:
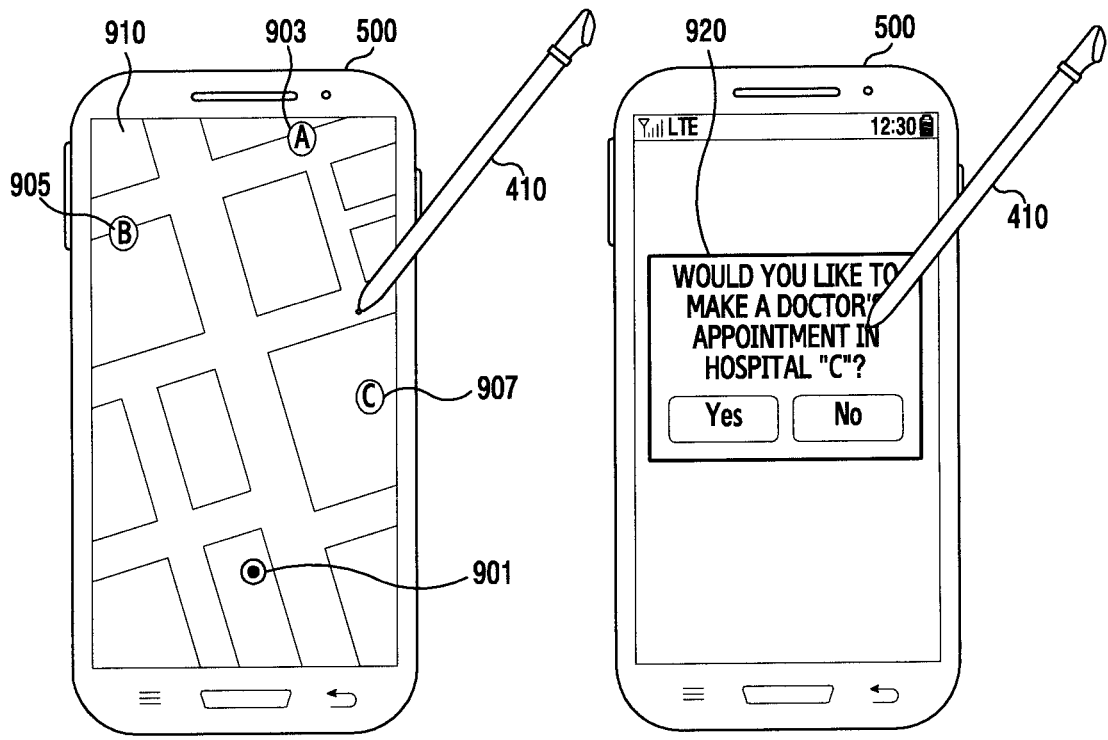
FIG. 9A, FIG. 9B, FIG. 9C and FIG. 9D are diagrams illustrating screens which show the operations of an electronic device to provide a service according to an embodiment of the present disclosure.

In operation 807, the electronic device (e.g., the processor 570) displays the location of the retrieved place (e.g., hospital). For example, this may be illustrated as shown in FIG. 9A. As illustrated in FIG. 9A, the electronic device (e.g., the processor 570) may display, in a display unit (e.g., the display unit 550), map data 910 including a present location 901 of the electronic device (e.g., the electronic device 500). The electronic device (e.g., the processor 570) may display hospital A 903, B 905, and C 907 that are located within a radius of about 2 Km based on the present location 901.

In operation 809, the electronic device (e.g., the processor 570) performs operation 811 when a reservation signal is received. When hospital C 907 is selected in FIG. 9A, the electronic device (e.g., the processor 570) may display a message 920 that facilitates scheduling of a doctor's appointment in the hospital C 907 as illustrated in FIG. 9B. When a hospital selection signal is not received during a predetermined period of time in FIG. 9A or when "No" is selected in the message 920 in operation 809, the electronic device (e.g., the processor 570) may terminate the process.

Figures 9C, 9D:
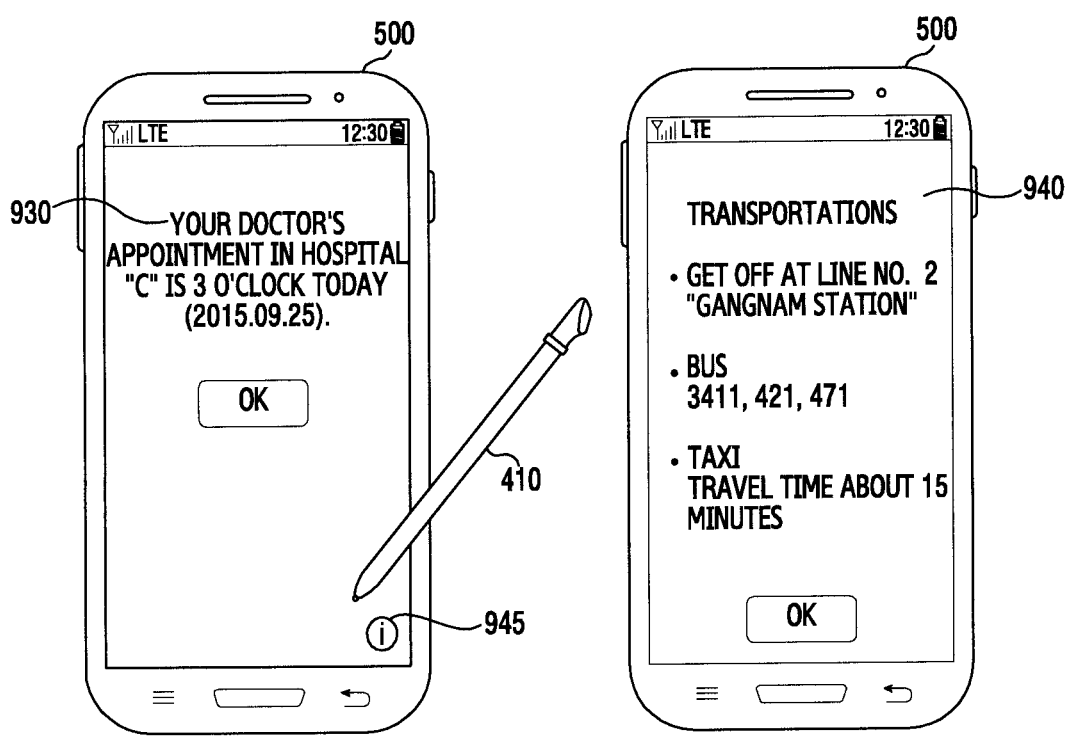

In operation 811, the electronic device (e.g., the processor 570) makes a reservation for medical treatment in hospital based on the reservation signal. For example, when "Yes" is selected in the message 920 displayed in FIG. 9B, the electronic device (e.g., the processor 570) may access a homepage or a reservation service operated by the hospital C 907. The electronic device (e.g., the processor 570) may display a screen associated with a reservation service, and may schedule a reservation for medical treatment in a hospital based on an input reservation date, an input reservation time, and the like. When the reservation for medical treatment is completed, the electronic device (e.g., the processor 570) may display a confirmation message 930 associated with the reservation as illustrated in FIG. 9C. For example, a reservation date, a reservation time, and the like are displayed in the message 930. According to an embodiment of the present disclosure, when an icon 945 corresponding to "i" is selected in FIG. 9C, the electronic device (e.g., the processor 570) may determine transportation from the present location 901 to the hospital C 907 for which the reservation is made. The electronic device (e.g., the processor 570) may display the determined transportation as illustrated in a message 940 of FIG. 9D. According to an embodiment of the present disclosure, the electronic device (e.g., the processor 570) may transmit sensing information (e.g., a body temperature measurement value) to a corresponding hospital when a reservation for medical treatment is made.

According to an embodiment of the present disclosure, at least one operation out of operations 801 to 813 may be omitted, or the order of operations may be changed. For example, operations 809 to 811 may be omitted. Also, for example, operation 813 may be omitted. Accordingly, when sensing information is included in a designated range in operation 801, the electronic device may not store sensing information.

Figure 10:
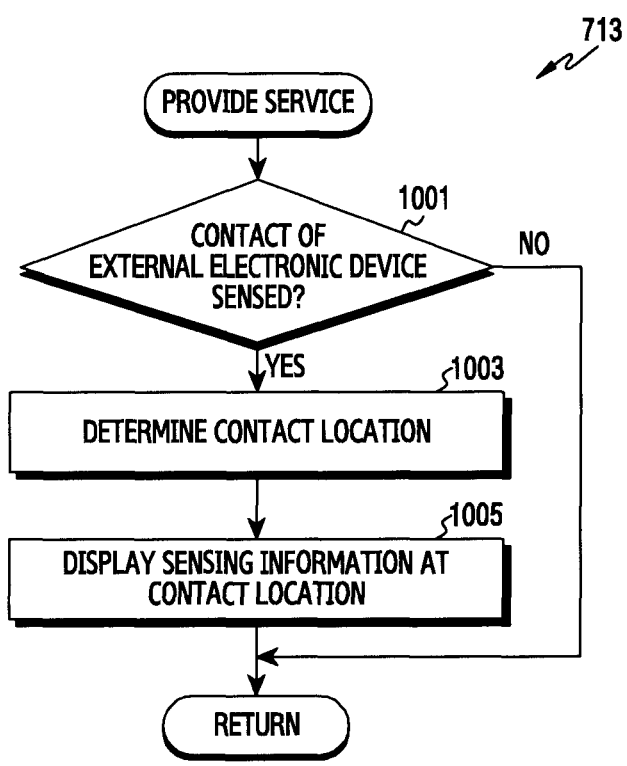
FIG. 10 is a flowchart illustrating operations of an electronic device to provide a service according to various embodiments of the present disclosure.

FIG. 10 is a flowchart illustrating operations of an electronic device to provide a service according to various embodiments of the present disclosure. FIG. 11 is a diagram illustrating a screen which shows the operations of an electronic device to provide a service according to various embodiments of the present disclosure. According to an embodiment of the present disclosure, operations 1001 to 1005 may be executed through an electronic device (e.g., the electronic device 101, 201, or 500) or a processor of the electronic device (e.g., the processor 120, 210, or 570, or a sensor manager).

Referring to FIGS. 10 to 11, the electronic device (e.g., the processor 570) detected whether the external electronic device 600 (e.g., a stylus pen, a headset, or a watch) is in contact with a display (e.g., the display unit 550) of the electronic device in operation 1001. For example, in operation 1001, when the external electronic device 600 (e.g., the stylus pen 410) is detected as being in contact with the display unit, the electronic device 500 (e.g., the processor 570) may perform operation 1003. In operation 1001, when the contact of the external electronic device 600 (e.g., the stylus pen 410) is not detected as being in contact with the display, the electronic device 500 (e.g., the processor 570) may execute some other function or terminate the process.

In operation 1003, the electronic device 500 (e.g., the processor 570) determines a contact location where the external electronic device 600 (e.g., the stylus pen 410) is in contact with the display unit. For example, the electronic device 500 (e.g., the processor 570) may determine a location where a change is detected in capacitance or electromagnetic field, which occurs as a result of the contact of the external electronic device 600 (e.g., the stylus pen 410) with the display. In operation 1005, the electronic device 500 (e.g., the processor 570) displays sensing information (e.g., a user's heartbeat information of 80), which is detected by the extracted electronic device 600 (e.g., the stylus pen 410), in a location 1101 where the external electronic device 600 (e.g., the stylus pen 410) is in contact, as illustrated in FIG. 11.

FIGS. 8 and 9 describe a service that provides information associated with a hospital that is close to the present location of a user based on the body temperature measurement value of the user who holds the external electronic device 600 (e.g., the stylus pen 410), from among the health information of the user. FIGS. 10 and 11 describe a service that provides the heart rate of a user who holds the external electronic device 600 (e.g., the stylus pen 410), from among the health information of the user. In various embodiments of the present disclosure, the service associated with the health of the user may not be limited to FIGS. 8 to 11.

According to an embodiment of the present disclosure, the electronic device 500 (e.g., the processor 570) uses sensing information (e.g., biometric information) obtained in the external electronic device 600 (e.g., the stylus pen 410), and determines the disease of a user or some condition, malady or other information that indicates that health treatment or care should be implemented. For example, based on sensing information (biometric information), the electronic device 500 (e.g., the processor 570) may determine, using the sensing information (e.g., the biometric information) a breathing rate, a heart rate, a heart rate variability, a blood oxygen saturation, a pulse rate, an irregular pulse, stress, blood pressure, resistance on the skin, body temperature, a skin moisture ratio, blood sugar, halitosis, an alcohol level, an acetone level, or the like. According to an embodiment of the present disclosure, the electronic device 500 (e.g., the processor 570) may determine an item that may require health care from the determined sensing information (e.g., biometric information), and provides the same to the user. For example, when the blood pressure of the user is high, the electronic device 500 (e.g., the processor 570) displays, in a display unit (e.g., the display unit 550), a message indicating that the user's detected blood pressure is higher than a normal recommended blood pressure level. For example, the electronic device 500 (e.g., the processor 570) may provide a notification in the form of a message in the display unit (e.g., the display unit 550) prompting the user to regularly exercise at a predetermined time, and may thereby provide a notification at a predetermined time through an output device (e.g., a speaker which is not illustrated and/or other like devices) implemented with the electronic device 500. The electronic device 500 (e.g., the processor 570) may provide a control signal to the external electronic device 600 (e.g., the stylus pen 410) so that the external electronic device COO (e.g., the stylus pen 410) outputs vibrations.

For example, the electronic device 500 (e.g., the processor 570) may provide information utilized for a user who has high blood pressure. For example, the electronic device 500 (e.g., the processor 570) may provide a user with various contents, such as a blood pressure-specialized health center, a diet providing application, a recipe providing application, an exercise guide providing application, or a link of a website including information utilized for managing blood pressure, an advertisement of a supplement for decreasing blood pressure, and the like. The electronic device 500 (e.g., the processor 570) may map the biometric information of the user and a time and a location where the biometric information is obtained, and may store the same.

For example, the electronic device 500 (e.g., the processor 570) may calculate the amount of exercise of a user, the amount of calorie consumed, or the like by interworking with a sporting equipment control device. The electronic device 500 (e.g., the processor 570) may additionally provide the user with the amount of calorie to be consumed, the speed of exercise, and the like, based on the calculated amount of exercise or the amount of calorie consumed.

FIG. 12 is a flowchart illustrating operations of an electronic device to provide a service according to various embodiments of the present disclosure. FIGS. 13A and 13B are diagrams illustrating screens which show the operations of an electronic device to provide a service according to various embodiments of the present disclosure. According to an embodiment of the present disclosure, operations 1201 to 1209 may be executed through an electronic device (e.g., the electronic device 101, 201, or 400) or a processor of the electronic device (e.g., the processor 120, 210, or 570, the program module 310, or a sensor manager).

Referring to FIGS. 12 and 13, the electronic device 500 (e.g., the processor 570) stores, in a memory (e.g., the memory 560), sensing information (e.g., a stress measurement value) received from the external electronic device 600 (e.g., the stylus pen 410) in operation 1201. In operation 1203, the electronic device 500 (e.g., the processor 570) determines whether the sensing information (e.g., a stress measurement value) is indicated as falling within a designated or predetermined range (e.g., indicating a value greater than a threshold value). When the sensing information (e.g., stress measurement value) is included within the designated range (e.g., when the sensing information is greater than a threshold value) in operation 1203, the electronic device 500 (e.g., the processor 570) performs operation 1205. When the sensing information (e.g., stress measurement value) is out of the designated range (e.g., when the sensing information is less than a threshold value) in operation 1203, the electronic device 500 (e.g., the processor 570) performs a corresponding function. The corresponding function may be a function that corresponds to an input from the external electronic device 600 (e.g., the stylus pen 410).

In operation 1205, the electronic device (e.g., the processor 570) displays a notification associated with whether to utilize or enable a service addressing a malady indicating by the sensing information (e.g., a color therapy service). For example, the electronic device 500 (e.g., the processor 570) may display a message 1310 facilitating selection/activation of a color therapy service in a display unit (e.g., the display unit 550), as illustrated in FIG. 13A. For example, when "Yes" is selected in the message 1310 that is displayed in the display unit (e.g., the display unit 550) as illustrated in FIG. 13A in operation 1207, the electronic device 500 (e.g., the processor 570) performs operation 1209.

In operation 1209, the electronic device 500 (e.g., the processor 570) provides the service (e.g., the color therapy service), and displays information (e.g., color) corresponding to the service of the display unit (e.g., the display unit 550). For example, the electronic device 500 (e.g., the processor 570) may change an entire color 1320 of the display unit (e.g., the display unit 550) as illustrated in FIG. 13B. For example, the electronic device 500 (e.g., the processor 570) may change the entire color 1320 into any one of various colors, such as blue, red, yellow, and the like, so as to correspond to a stress measurement value. According to various embodiments of the present disclosure, at least one operation out of operations 1201 to 1209 may be omitted, or the order of operations may be changed. For example, operations 1205 to 1207 may be omitted. Accordingly, when the sensing information is included in the designated range in operation 1203, the electronic device 500 provides a service in operation 1209.

FIGS. 12 and 13 describe a service that controls a User Interface (UI) of the electronic device 500, from among controlling of the electronic device. According to various embodiments of the present disclosure, a service associated with controlling the electronic device 500 may not be limited to FIGS. 12 and 13.

According to an embodiment of the present disclosure, the electronic device 500 (e.g., the processor 570) may change the property of an input of the external electronic device 600 (e.g., the stylus pen 410), may change the layout of an input of the external electronic device 600 (e.g., the stylus pen 410), or may insert sensing information (e.g., biometric information) to a content that a user currently writes, based on the sensing information (e.g., biometric information) obtained in the external electronic device 600 (e.g., the stylus pen 410). For example, the electronic device 500 (e.g., the processor 570) may determine, from the biometric information, the emotion of a user, including nerves, excitement, calm, or the like. The electronic device 500 (e.g., the processor 570) may change the properties of an input of the external electronic device 600 (e.g., the stylus pen 410), such as color, thickness, texture, or the like, based on the determined emotion. The electronic device 500 (e.g., the processor 570) may change the layout when the external electronic device 600 (e.g., the stylus pen 410) is used, such as the disposition of icons or the like, based on the determined emotion. The electronic device 500 (e.g., the processor 570) may add, for example, an emoticon, and the like, to a diary that is currently written a text message, or an image obtained through a camera, based on the emotion of the user.

According to an embodiment of the present disclosure, the electronic device 500 (e.g., the processor 570) may determine the age band of a user based on the obtained biometric information. According to an embodiment of the present disclosure, the electronic device 500 (e.g., the processor 570) may correct input text through the external electronic device 600 (e.g., the stylus pen 410) based on the determined age band. According to an embodiment of the present disclosure, the electronic device 500 (e.g., the processor 570) may change a UI theme of the electronic device 500 based on the determined age band. For example, the electronic device 500 (e.g., the processor 570) may enlarge an icon, characters, and the like based on the age band, and may display the same.

According to an embodiment of the present disclosure, the electronic device 500 (e.g., the processor 570) may control a peripheral electronic device using the obtained sensing information (e.g., biometric information). The electronic device 500 (e.g., the processor 570) may control a peripheral electronic device, such as an air conditioner, a lighting installation, an audio device, a control device of sporting equipment, and the like, based on the sensing information biometric information). For example, when the body temperature of the user is out of a normal range, the electronic device 500 (e.g., the processor 570) controls a peripheral electronic device; for example, controlling the air conditioner so as to raise room temperature.

According to an embodiment of the present disclosure, the electronic device 500 (e.g., the processor 570) may determine the stress index of a user based on sensing information (e.g., biometric information). According to an embodiment of the present disclosure, when the stress index is out of the normal range, the electronic device 500 (e.g., the processor 570) may provide a user with a warning alarm so as to restrain the use of the electronic device 500. According to an embodiment of the present disclosure, when the stress index is out of the normal range, the electronic device 500 (e.g., the processor 570) may provide a user with a picture or the like for stress treatment, so as to decrease the stress index through painting the picture.

FIG. 14 is a flowchart illustrating operations of an electronic device to provide a service according to various embodiments of the present disclosure. FIGS. 15A to 15C are diagrams illustrating screens which show the operations of an electronic device to provide a service according to various embodiments of the present disclosure. According to an embodiment of the present disclosure, operations 1401 to 1407 may be executed through an electronic device (e.g., the electronic device 101, 201, or 400) or a processor of the electronic device (e.g., the processor 120, 210, or 570, the program module 310, or a sensor manager).

Referring to FIGS. 14 and 15, the electronic device 500 (e.g., the processor 570) provides sensing information (e.g., biometric information) received from the external electronic device 600 (e.g., the stylus pen 410) to an external device (e.g., an external server that utilizes user authentication) in operation 1401. In operation 1403, the electronic device 500 (e.g., the processor 570) determines whether authentication based on the sensing information (e.g., biometric information) is successful. If authentication is unsuccessful in operation 1403, the electronic device 500 performs operation 1407 when user authentication fails based on the provided sensing information (e.g., biometric information). In operation 1407, the electronic device 500 (e.g., the processor 570) displays, in a display unit (e.g., the display unit 550), a message indicating that user authentication has failed.

If authentication is successful in operation 1403, the electronic device 500 (e.g., the processor 570) performs operation 1405 in which the electronic device 500 (e.g., the processor 570) transmits data to a designated external device (e.g., a server, for example, an external server that performs user authentication). For example, as illustrated in FIG. 15A, the electronic device 500 (e.g., the processor 570) may select, from a file list 1501, a file to be transmitted to the external device (e.g., a server). The electronic device 500 (e.g., the processor 570) transmits sensing information e.g., biometric information) to the external device (e.g., a server) when a predetermined file is selected from the file list 1501. For example, when user authentication is successfully performed based on the sensing information (e.g., biometric information), the electronic device 500 may display, in a display unit (e.g., the display unit 550), a message 1510 indicating that authentication is successfully performed, as illustrated in FIG. 15B. The electronic device 500 (e.g., the processor 570) transmits the selected predetermined file to a designated location of the external device (e.g., server) when "Yes" is selected in the message 1510. When file transmission to the external device (e.g., server) is completed, the electronic device 500 (e.g., the processor 570) may display, in the display unit (e.g., the display unit 550), a message 1520 indicating that storing the file in the designated location is completed, as illustrated in FIG. 15C.

FIGS. 14 and 15 describe a service that transmits data stored in the electronic device 500 to an external server, and stores the same, even during user authentication. In the present disclosure, the user authentication service may not be limited to FIGS. 14 and 15.

According to an embodiment of the present disclosure, the electronic device 500 (e.g., the processor 570) uses sensing information (e.g., biometric information) obtained in the external electronic device 600 (e.g., the stylus pen 410), to identify a user. For example, the electronic device 500 (e.g., the processor 570) may identify a user based on an electrocardiogram (ECG) waveform, a pulse waveform, a breathing rate, or the like, which is different for each user. For example, in the case that utilizes security or authentication, such as financial transaction, web login, and the like, the electronic device 500 (e.g., the processor 570) may perform user authentication using a signature and biometric information of a user.

According to an embodiment of the present disclosure, the electronic device 500 (e.g., the processor 570) may identify a user based on sensing information (e.g., biometric information), and provides a personalized UI based on a result of identification. When a plurality of inputs are provided to the electronic device 500 through a plurality of external electronic devices 600 (e.g., the stylus pen 410), the electronic device 500 (e.g., the processor 570) may identify a user based on biometric information, and may simultaneously process the plurality of inputs of the plurality of external electronic devices 600 (e.g., the stylus pen 410), FIG. 16 is a flowchart illustrating operations of an electronic device to provide a service according to various embodiments of the present disclosure. According to an embodiment of the present disclosure, operations 1601 to 1607 may be executed through an electronic device (e.g., the electronic device 101, 201, or 400) or a processor of the electronic device e.g., the processor 120, 210, or 570, the program module 310, or a sensor manager).

Referring to FIG. 16, in operation 1601, the electronic device 500 (e.g., the processor 570) stores, in a memory (e.g., the memory 560), sensing information (e.g., the health condition of a user, concentration, fatigability, or a stress index) received from the external electronic device 600 (e.g., the stylus pen 410). In operation 1603, the electronic device 500 (e.g., the processor 570) displays a notification whether to use a service (e.g., a learning process plan, a personalized learning, a user's health care service, such as stress controlling, or the like), based on the stored sensing information.

In operation 1605, the electronic device 500 (e.g., the processor 570) performs operation 1607 when a selection is detected indicating a service to be provided (e.g., a learning process plan, a personalized learning, a user's health care service, such as stress controlling, or the like), which may be provided by, for example, a user input. In operation 1605, if a provided service (e.g., a learning process plan, a personalized learning, a user's health care service, such as stress controlling, or the like) is not selected, the electronic device 500 (e.g., the processor 570) may perform a corresponding function. The corresponding function may be a function that corresponds to an input from the external electronic device 600 e.g., the stylus pen 410).

In operation 1607, in response to a selection to provide the service, the electronic device 500 (e.g., the processor 570) provides the service (e.g., a learning process plan, a personalized learning, a user's health care service, such as stress controlling, or the like), and displays information corresponding to the provided service of a display unit (e.g., the display unit 550). In operation 1607, the electronic device 500 (e.g., the processor 570) provides an e-school service (e.g., online learning and education) using sensing information (e.g., user's health condition, concentration, fatigability, or a stress index) accumulated in operation 1601. The electronic device 500 (e.g., the processor 570) may determine a time when a user has high concentration based on the accumulated sensing information (e.g., user's health condition, concentration, fatigability, or a stress index). The electronic device 500 (e.g., the processor 570) may provide a user with the determined time, and may reflect the determined timetable in a schedule.

An operation method of the electronic device 500, according to an embodiment of the present disclosure, may include: determining an application executed in the electronic device 500; when the application is a first application, transmitting first information corresponding to the first application to an accessory device (e.g., the stylus pen 410) including a first sensor and a second sensor; when the application is a second application, transmitting second information corresponding to the second application to an accessory device (e.g., the stylus pen 410); and receiving, from the accessory device (e.g., the stylus pen 410), data obtained through a sensor out of the first sensor and the second sensor, which corresponds to information transmitted from among the first information and the second information.

According to various embodiments of the present disclosure, the operation of transmitting the information corresponding to the application may include: transmitting the information to the accessory device (e.g., the stylus pen 410) based on at least some of a situation in which the accessory device (e.g., the stylus pen 410) is separated from the electronic device 500.

According to various embodiments of the present disclosure, an operation of displaying an object for inputting data in a display (e.g., the display unit 550) included in the electronic device 500; and an operation of displaying the received data in a corresponding area based on at least some of a situation in which at least a part of the accessory device (e.g., the stylus pen 410) is in contact with an area of the display which corresponds to the object, may be further included.

Figure 17:
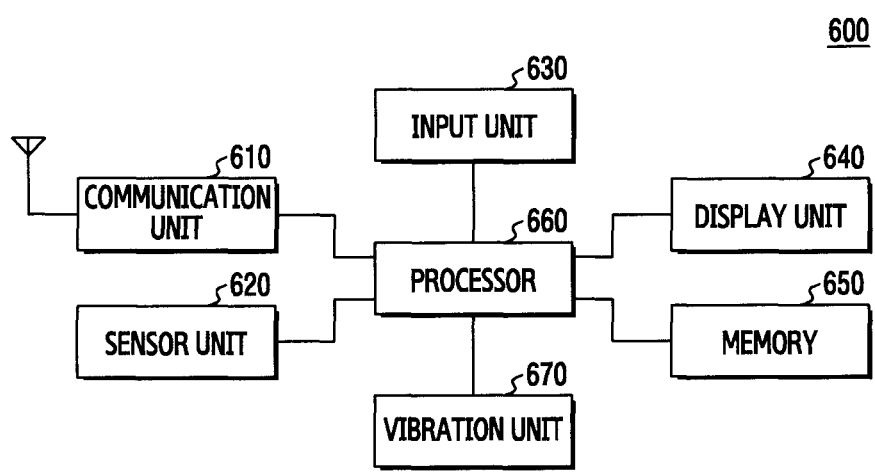
FIG. 17 is a block diagram illustrating a configuration of an external electronic device according to an embodiment of the present disclosure.

FIG. 17 is a block diagram illustrating a configuration of an external electronic device (e.g., a stylus pen) according to an embodiment of the present disclosure.

Referring to FIG. 17, the electronic device 600 (e.g., the electronic device 101 or 201, or the stylus pen 410) may include: the communication unit 610 (e.g., the communication interface 170, the communication module 220, and the interface 270); the sensor unit 620 (e.g., the sensor module 240); the input unit 630 (e.g., the input/output interface 150, the input device 250, the audio module 280, the speaker 282, the receiver 284, the earphones 286, the microphone 288, the camera module 291, the indicator 297, or the motor 298); the display unit 640 (e.g., the display 160 or the display 260), the memory 650 (e.g., the memory 130 or the memory 230); and the processor 660 (e.g., the processor 120, the processor 210, the program module 310, or a sensor manager). According to various embodiments of the present disclosure, the communication unit 610, the sensor unit 620, the input unit 630, the display unit 640, the memory 650, or the processor 660 may be included in the single external electronic device 600 or a plurality of different external electronic devices.

According to an embodiment of the present disclosure, the communication unit 610 may perform communication with another electronic device (e.g., the electronic device 500). For example, the communication unit 610 may perform communication with another electronic device (e.g., the electronic device 500) in various schemes. The communication unit 610 may perform communication with another electronic device (e.g., the electronic device 500) through short-range wireless communication, such as Bluetooth, Near Field Communications (NFC), or Infrared Ray (IR), or the like. The communication unit 610 may perform communication with another electronic device (e.g., the electronic device 500) through Electronic Magnetic resonance (EMR).

When the sensor unit 620 is detached from the other electronic device (e.g., the electronic device 500), the sensor unit 620 may be activated under the control of the processor 660. The sensor unit 620 may activate a sensor associated with an application, based on information associated with the application that is received from the other electronic device (e.g., the electronic device 500) through the communication unit 610. The sensor unit 620 may transfer the sensing information to the processor 660. The sensor unit 620 may include at least one sensor from among the sensors listed in Table 1 as provided below. Each sensor may obtain sensing information as shown in Table 1. Various types of services may be provided to a user using each piece of sensing information. The sensor unit 620 may further include an acceleration sensor, a gyro sensor, or a pressure sensor, and the like.

According to an embodiment of the present disclosure, referring to Table 1, the sensor unit 620 may be a heart rate monitor sensor. The heart rate monitor sensor may obtain a heart rate, a breathing rate, a heart rate variability, or a blood oxygen saturation. The electronic device 600 may provide an exercise guide service, a health guide service, or a stress guide service, based on sensing information obtained through the heart rate monitor sensor.

According to an embodiment of the present disclosure, referring to Table 1, the sensor unit 620 may be an ECR monitor sensor. The ECR monitor sensor may obtain a pulse rate, an irregular pulse, stress, or a heart rate variability. The electronic device 600 may provide a health guide using an irregular pulse, an authentication service, or a stress guide service, based on sensing information obtained through the ECR rate monitor sensor.

According to an embodiment of the present disclosure, referring to Table 1, the sensor unit 620 may be a heart rate monitor sensor and an ECR monitor sensor. The heart rate monitor sensor and the ECR monitor sensor may obtain blood pressure. The electronic device 600 may provide a health information providing service using sensing information that is obtained through the heart rate monitor sensor and the ECR monitor sensor.

According to an embodiment of the present disclosure, referring to Table 1, the sensor unit 620 may be a sensor for an electric impedance of the skin. The sensor for an electric impedance of the skin may obtain resistance on the skin. The electronic device 600 may provide an emotion and stress guide service based on sensing information obtained through the sensor for an electric impedance of the skin.

According to an embodiment of the present disclosure, referring to Table 1, the sensor unit 620 may be a thermometer. The thermometer may obtain the body temperature of a user. The electronic device 600 may provide a health guide service or an external device control guide service based on sensing information obtained through the thermometer.

According to an embodiment of the present disclosure, referring to Table 1, the sensor unit 620 may be a skin hydration degree sensor. The skin hydration degree sensor may obtain the degree of hydration of the skin. The electronic device 600 may provide a skin care guide service based on sensing information obtained through the skin hydration degree sensor.

According to an embodiment of the present disclosure, referring to Table 1, the sensor unit 620 may be a blood sugar sensor. The blood sugar sensor may obtain a blood sugar level of a user. The electronic device 600 may provide a diabetes control service based on sensing information obtained through the blood sugar sensor.

According to an embodiment of the present disclosure, referring to Table 1, the sensor unit 620 may be a gas sensor. The gas sensor may obtain halitosis, an alcohol level, or an acetone level. The electronic device 600 may provide a drinking control service, an obesity control service, or diseases-related breathing analysis service, based on sensing information obtained through the gas sensor.

According to an embodiment of the present disclosure, referring to Table 1, the sensor unit 620 may be an ultraviolet ray sensor. The ultraviolet ray sensor may obtain the intensity of ultraviolet rays. The electronic device 600 may provide a skin protection guide service based on sensing information obtained through the ultraviolet ray sensor.

According to an embodiment of the present disclosure, referring to Table 1, the sensor unit 620 may be an illuminance sensor. The illuminance sensor may obtain the intensity of light. The electronic device 600 may provide a brightness control service associated with the display unit (e.g., the display unit 550) of another electronic device (the electronic device 500), may provide a fatigability guide service by accumulating the amount of light exposure, or may provide an external device control guide service, using sensing information obtained through the illuminance sensor.

According to an embodiment of the present disclosure, referring to Table 1, the sensor unit 620 may be a speaker. The speaker may obtain sound. The electronic device 600 may measure snoring during sleep using sound obtained through the speaker, and may provide a health guide service.

TABLE 1

| Type of Sensor | Sensing Information | Service |
|---|---|---|
| Heart rate monitor sensor | Heart rate, Breathing rate, | exercise guide service using blood oxygen saturation |

TABLE 1-continued

| Type of Sensor | Sensing Information | Service |
|---|---|---|
| | Heart rate variability, Blood oxygen saturation | exercise guide service, health guide service, and stress guide service using breathing rate and heart rate |
| ECR monitor sensor | Pulse rate, Irregular pulse, Stress, Heart rate variability | health guide using irregular pulse authentication service stress guide |
| Heart rate + ECR monitor sensor | Blood pressure | health information providing service |
| Sensor for electric impedance of skin | Resistance on skin | emotion and stress guide service |
| Thermometer | Body temperature | health guide service external device control guide service |
| Skin hydration degree sensor | Degree of hydration of skin | skin care guide service |
| Blood sugar sensor | Sugar level | diabetes control service |
| Gas sensor | Halitosis, alcohol level, acetone level | drinking control service obesity control service diseases-related breathing analysis service |
| Ultraviolet ray sensor | Intensity of ultraviolet ray | skin protection guide service |
| Illuminance sensor | Intensity of light | brightness control service associated with a display unit (e.g., the display unit 550) of of another electronic device (the electronic device 500) fatigability guide service by accumulating the amount of light exposure external device control guide service |
| Speaker | sound | health guide service by measuring snoring in sleep. |

According to an embodiment of the present disclosure, the input unit 630 may generate input data corresponding to a user input of the external electronic device 600 (e.g., the stylus pen 410). The input unit 630 may include at least one input means. The input unit 630 may include, for example, a physical button or the like. According to an embodiment of the present disclosure, the input unit 630 may transfer a user input to the processor 660.

According to an embodiment of the present disclosure, the display unit 640 may display the state of an external electronic device (e.g., the stylus pen 410), including a battery charging state, a sensing state, or whether communication with another electronic device (e.g., the electronic device 500) is executed. For example, the display unit 640 may display sensing information obtained by the external electronic device (e.g., the stylus pen 410). To this end, the display unit 640 may include a Liquid Crystal Display (LCD), a Light Emitting Diode (LED) display, an Organic LED (OLED) display, a Micro Electro Mechanical System (MEMS) display, and an electronic paper display. The display unit 640 may include, for example, a plurality of light emitting devices.

According to an embodiment of the present disclosure, the display unit 640 may display a residual quantity of battery power under the control of the processor 660. The display unit 640 may display different colors based on a residual quantity of battery power, and may display the residual quantity of battery power when the residual quantity is less than, or equal to, a predetermined residual quantity.

According to an embodiment of the present disclosure, the memory 650 may store operating programs of the electronic device 600 (e.g., the stylus pen 410). The memory 650 may store information associated with the external electronic device 600 (e.g., the stylus pen 410), such as a manufacturer, a manufacturing date, identification information, or the like.

According to an embodiment of the present disclosure, the processor 660 may activate a sensor corresponding to information associated with an application, which is received from another electronic device (e.g., the electronic device 500). The processor 660 may transmit data (hereinafter, sensing information) obtained from the activated sensor to another electronic device (e.g., the electronic device 500). The external electronic device 600 (e.g., the stylus pen 410) may transmit sensing information to another electronic device (e.g., the electronic device 500) using short-range wireless communication. Also, when the tip of the external electronic device 600 (e.g., the stylus pen 410) is in contact with the display unit 550 of another electronic device (e.g., the electronic device 500), the external electronic device 600 (e.g., the stylus pen 410) may transmit sensing information to the other electronic device (e.g., the electronic device 500) through an EMR scheme.

According to an embodiment of the present disclosure, the processor 660 may transmit sensing information sensed by the external electronic device 600 (e.g., the stylus pen 410) to another electronic device (e.g., the electronic device 500) when a predetermined condition is satisfied. The predetermined condition may be one out of: a point in time when sensing information is sensed; a point in time when a predetermined period arrives; a point in time when an input is provided in the external electronic device 600 (e.g., the stylus pen 410); a point in time when a touch occurs in another electronic device (e.g., the electronic device 500); a point in time when a predetermined application is executed in another electronic device (e.g., the electronic device 500); a point in time when sensing information that satisfies a predetermined standard is sensed; a point in time when the screen of another electronic device (e.g., the electronic device 500) is on/off; and a point in time when the external electronic device 600 (e.g., the stylus pen 410) is inserted into another electronic device (e.g., the electronic device 500).

Although embodiments of the present disclosure describe that a corresponding sensor is activated when application information is received from another electronic device (e.g., the electronic device 500), the present disclosure may not be limited thereto. A sensor included in the external electronic device 600 (e.g., the stylus pen 410) may be activated every time that a point in time when an input is provided in the external electronic device 600 (e.g., the stylus pen 410), a point in time when the external electronic device 600 (e.g., the stylus pen 410) is detached from another electronic device (e.g., the electronic device 500), a point in time when the external electronic device 600 (e.g., the stylus pen 410) is held, a point in time when the movement of the external electronic device 600 (e.g., the stylus pen 410) is sensed, or a point in time when a predetermined period arrives. Any one of a sensor that is capable of sensing whether the external electronic device 600 (e.g., the stylus pen 410) is held and a movement sensor is activated from among the sensors included in the external electronic device 600 (e.g., the stylus pen 410).

Although not illustrated, according to an embodiment of the present disclosure, the external electronic device 600 (e.g., the stylus pen 410) may include a ground for charging a battery. For example, the external electronic device 600 (e.g., the stylus pen 410) may include two grounds for power and ground (GND), for charging a battery. Also, for example, the external electronic device 600 (e.g., the stylus pen 410) may additionally include a ground for determining a property of the external electronic device 600 (e.g., the stylus pen 410), and may additionally include a ground for the communication with another electronic device (e.g., the electronic device 500). For example, the external electronic device 600 (e.g., the stylus pen 410) may reveal at least one out of the grounds for charging only when the external electronic device 600 is installed to another electronic device (e.g., the electronic device 500). For example, a pogo pin may be included in the tip of the electronic device 600 (e.g., the stylus pen 410) or in the center of the external electronic device 600 (e.g., the stylus pen 410). For example, the ground for charging may be in the form of a ring that encloses the external electronic device 600 (e.g., the stylus pen 410).

According to an embodiment of the present disclosure, the vibration unit 670 may include a vibration motor. The vibration unit 670 may generate, under the control of the processor 660, vibrations and may provide the vibrations to a user who holds the external electronic device 600 (e.g., the stylus pen 410).

An electronic device (e.g., the external electronic device 600 or the stylus pen 410), according to an embodiment of the present disclosure, may include: a first sensor for obtaining first data, a second sensor for obtaining second data, a communication interface (e.g., the communication unit 610), and a processor (e.g., the processor 660). The processor (e.g., the processor 660) may be configured to: receive, from an external electronic device (e.g., the electronic device 500), information corresponding to an application that is executed in the external electronic device 500; obtain the first data through the first sensor when the information is first information; obtain the second data through the second sensor when the information is second information; and transmit, to the external electronic device (e.g., the electronic device 500), obtained data from among the first data and the second data.

According to various embodiments of the present disclosure, the processor (e.g., the processor 660) may be configured to: activate the first sensor and deactivate the second sensor when the information is the first information; deactivate the first sensor and activate the second sensor when the information is the second information; and use an activated sensor out of the first sensor and the second sensor, and obtain data corresponding to the activated sensor out of the first data and the second data.

According to various embodiments of the present disclosure, the processor (e.g., the processor 660) may be configured to receive information based on at least some of a situation in which the electronic device 600 and the external electronic device 500 are physically separated.

According to various embodiments of the present disclosure, the first data or the second data may include biometric data.

According to various embodiments of the present disclosure, the processor (e.g., the processor 660) may be configured to transmit data to the external electronic device 500 based on at least some of a situation in which the electronic device 600 is in contact with a touch screen included in the external electronic device 500.

According to various embodiments of the present disclosure, the processor (e.g., the processor 660) is configured to: receive a request for the first data as at least a part of the information when the application is a first application; and receive a request for the second data as at least a part of the information when the application is a second application.

According, to various embodiments of the present disclosure, the processor (e.g., the processor 660) may be configured to transmit data to the external electronic device 500 so that biometric information corresponding to the data is displayed through a display included in the external electronic device 500.

According to various embodiments of the present disclosure, the electronic device 600 may be an accessory device of the external electronic device 500 that includes the stylus pen 410.

Figure 18:
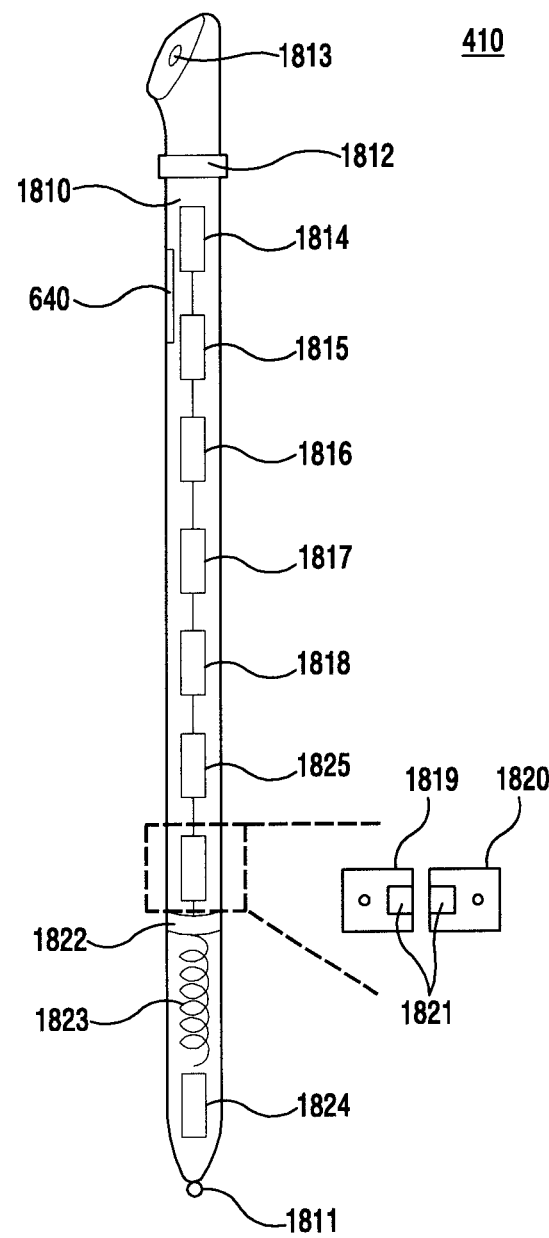
FIG. 18 is a perspective view of a stylus pen according to an embodiment of the present disclosure.

FIG. 18 is a perspective view of a stylus pen according to an embodiment of the present disclosure.

Referring to FIG. 18, the stylus pen 410 (e.g., the external electronic device 600), according to various embodiments of the present disclosure, may include a plurality of sensors in a housing 1810. According to an embodiment of the present disclosure, a tip 1811 in which a pen tip and a pressure sensor are coupled may be included in one end of the stylus pen 410. For example, one end of the stylus pen 410 may be one end that may be inserted into a lateral side of the electronic device 500 when it is installed to the electronic device 500. For example, one end of the stylus pen 410 may be one end that may be in contact when a user holds the stylus pen 410. Although the present disclosure illustrates that the housing 1810 is in the form of a cylinder, the present disclosure may not be limited thereto.

For example, a thermometer, a skin hydration degree sensor, or a blood sugar sensor 1813 may be included in the other end of the stylus pen 410. For example, the other end of the stylus pen 410 may be one end that may be exposed from a lateral side of the electronic device 500 when it is installed to the electronic device 500. When only a thermometer is included in the other end of the stylus pen 410, the other end may be waterproofed.

According to an embodiment of the present disclosure, an insulating part 1812 may be formed in a position close to the other end of the stylus pen 410. For example, a plurality of components 1814, 1815, 1816, 1817, 1818, 1819, 1820, 1821, and 1823 may be sequentially disposed in the housing 1810 of the stylus pen 410. For example, the component 1814 out of the components disposed in the housing 1810 may be an acceleration sensor and a gyro sensor. For example, the component 1815 may be a battery. For example, the component 1816 may be the memory 650. For example, the component 1817 may be the processor 660. For example, the component 1818 may be a gas sensor. For example, the components 1819 to 1821 may be electrodes #1 and #2 of the ECR monitor sensor and a heart rate monitor sensor, respectively. For example, the component 1822 may be a sensor for electric impedance of the skin. For example, the component 1823 may be an EMR. For example, the component 1824 may be the electrode #3 of the ECR monitor sensor. For example, the component 1825 may be a vibration motor included in the vibration unit 670.

The electrode #1 1819 of the ECR monitor sensor, the electrode #2 1820 of the ECR monitor sensor, the heart rate monitor sensor 1821, the sensor 1822 for an electric impedance of the skin, or the electrode #3 1824 of the ECR monitor sensor of the stylus pen 410 may be disposed in the position of the stylus pen 410 that is held by a user. For example, the EMR 1823 may be disposed in a location where the EMR 1823 may be operated by a pressure provided to the tip 1811 in which a pen tip and a pressure sensor are coupled. According to various embodiments of the present disclosure, the disposition of the components 1813 to 1818 may be modified. The display unit (e.g., the display unit 640) may be formed outside the housing 1810 of the stylus pen 410.

Figure 19:
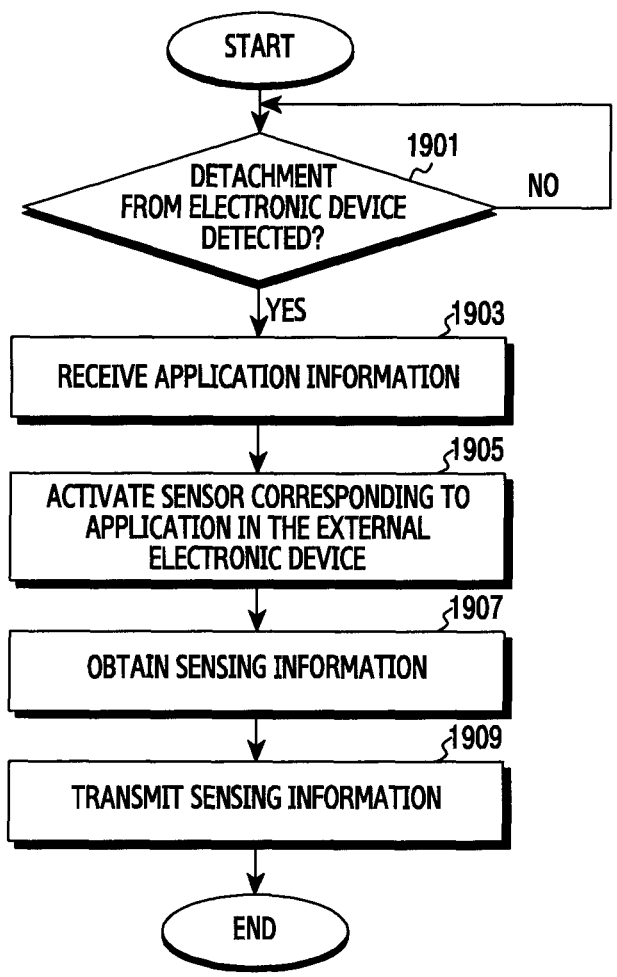
FIG. 19 is a flowchart illustrating operations of an external electronic device according to an embodiment of the present disclosure.

FIG. 19 is a flowchart illustrating operations of an external electronic device (e.g., a stylus pen) according to an embodiment of the present disclosure. According to an embodiment of the present disclosure, operations 1901 to 1909 may be executed through an electronic device (e.g., the electronic device 101, 201, or 600), the stylus pen 410, or a processor of the electronic device (e.g., the processor 120, 210, or 660, the program module 310, or a sensor manager).

Referring to FIG. 19, the external electronic device (e.g., the processor 660) may detect whether the external electronic device is detached from the electronic device (e.g., the electronic device 500) in operation 1901. According to an embodiment of the present disclosure, in operation 1903, if the external, electronic device is detected as detached, the external electronic device (e.g., the processor 660) may receive information corresponding to an application executed in the electronic device e.g., the electronic device 500) from the electronic device (e.g., the electronic device 500), in operation 1903. For example, the external electronic device (e.g., the processor 660) may activate a communication unit (e.g., the communication unit 610) when the external electronic device is detected as detached from the electronic device (e.g., the electronic device 500), and may then perform communication (e.g., short-range wireless communication) with the electronic device (e.g., the electronic device 500).

According to an embodiment of the present disclosure, the external electronic device (e.g., the processor 660) may activate a sensor corresponding to the received information corresponding to the application, in operation 1905. For example, the external electronic device (e.g., the processor 660) may include a first sensor and a second sensor. When the information corresponding to the application is first information, the external electronic device (e.g., the processor 660) may activate the first sensor. In this instance, the external electronic device (e.g., the processor 660) may deactivate the second sensor. Also, when the information corresponding to the application is second information, the external electronic device e.g., the processor 660) may activate the second sensor. In this instance, the external electronic device (e.g., the processor 660) may deactivate the first sensor.

The information corresponding to the application may include, for example, sensing information that is utilized to execute the application. For example, when the first application (e.g., a heart rate measuring application) is executed in the electronic device (e.g., the electronic device 500), the information corresponding to the application may include a request for first sensing information (e.g., heart rate information) utilized to execute the first application. Also, when the second application (e.g., an exercise application) is executed in the electronic device (e.g., the electronic device 500), the information corresponding to the application may include a request for second sensing information e.g., acceleration information) utilized to execute the second application.

According to an embodiment of the present disclosure, the external electronic device (e.g., the processor 660) may obtain sensing information from the activated sensor in operation 1907. For example, in the case of an external electronic device (e.g., the processor 660) including a first sensor and a second sensor, when the first sensor is activated, the external electronic device (e.g., the processor 660) may obtain data obtained through the first sensor as sensing information. Also, when the second sensor is activated, the external electronic device (e.g., the processor 660) may obtain data obtained through the second sensor as sensing information.

According to an embodiment of the present disclosure, the external electronic device (e.g., the processor 660) transmits the obtained sensing information to the electronic device (e.g., the electronic device 500) in operation 1909. For example, the external electronic device (e.g., the processor 660) may transmit, to the electronic device (e.g., the electronic device 500), sensing information through an EMR when the external electronic device (e.g., the tip 1811 of the stylus pen 410) is in contact with a display unit (e.g., the display unit 550) of the electronic device (e.g., the electronic device 500). The processor 660 may transmit sensing information to the electronic device 500 through short-range wireless communication.

According to an embodiment of the present disclosure, the sensing information transmitted from the external electronic device (e.g., the processor 660) may be displayed through the display unit (e.g., a display) included in the electronic device (e.g., the electronic device 500).

According to various embodiments of the present disclosure, at least one operation out of operations 1901 to 1909 may be omitted, or the order of operations may be changed. For example, operation 1901 may be omitted. Accordingly, the external electronic device (e.g., the stylus pen 410) may receive the application information in operation 1903, irrespective of whether the external electronic device is detached from the electronic device e.g., the electronic device 500).

Figure 20:
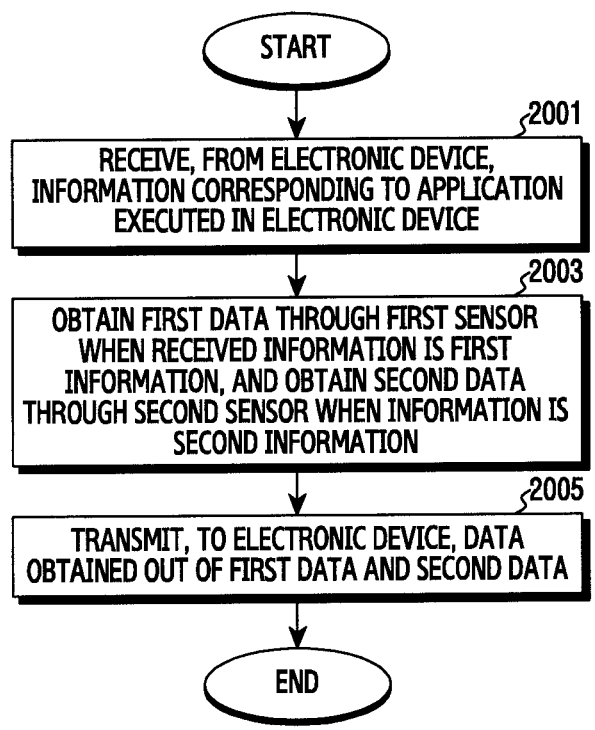
FIG. 20 is a flowchart illustrating operations of an external electronic device according to various embodiments of the present disclosure.

FIG. 20 is a flowchart illustrating operations of an external electronic device according to various embodiments of the present disclosure. According to an embodiment of the present disclosure, operations 2001 to 2003 may be executed through an electronic device (e.g., the electronic device 101, 201, or 600), the stylus pen 410, or a processor of the electronic device (e.g., the processor 120, 210, or 660, or a sensor manager).

Referring to FIG. 20, the external electronic device (e.g., the processor 660) may receive information corresponding to an application executed in the electronic device (e.g., the electronic device 500), from the electronic device (e.g., the electronic device 500), in operation 2001.

According to an embodiment of the present disclosure, in operation 2003, the external electronic device (e.g., the processor 660) obtains first data through a first sensor when the received information corresponding to the application is first information. Continuing in operation 2003, the external electronic device (e.g., the processor 660) may obtain second data through a second sensor when the received information corresponding to the application is second information.

According to an embodiment of the present disclosure, when the first data is obtained in operation 2003, the external electronic device (e.g., the processor 660) may transmit the first data to the electronic device (e.g., the electronic device 500) in operation 2005. When the second data is obtained in operation 2003, the external electronic device (e.g., the processor 660) may also transmit the second data to the electronic device (e.g., the electronic device 500) in operation 2005. The external electronic device (e.g., the processor 660) may transmit the data obtained in operation 2003 out of the first data and the second data to the electronic device (e.g., the electronic device 500) through an EMR when the external electronic device (e.g., the tip 1811 of the stylus pen 410) is in contact with a display unit (e.g., the display unit 550) of the electronic device (e.g., the electronic device 500). The processor 660 may transmit the data obtained in operation 2003 out of the first data and the second data to the electronic device 500 through short-range wireless communication.

According to an embodiment of the present disclosure, the data obtained in operation 2003 out of the first data and the second data, which are transmitted from the external electronic device (e.g., the processor 660), may be displayed through the display unit (e.g., a display) included in the electronic device (e.g., the electronic device 500).

An operation method of an external electronic device (e.g., stylus pen 410), according to various embodiments of the present disclosure, may include: receiving, from an electronic device (e.g., the electronic device 500), information corresponding to an application that is executed in the electronic device 500; obtaining first data through a first sensor when the information is first information; obtaining second data through a second sensor when the information is second information; and transmitting, to the electronic device 500, data obtained out of the first data and the second data.

According to various embodiments of the present disclosure, the operation of obtaining the first data through the first sensor may include: obtaining the first data by activating the first sensor and deactivating the second sensor when the information is the first information.

According to various embodiments of the present disclosure, the operation of obtaining the second data through the second sensor may include: obtaining the second data by deactivating the first sensor and activating the second sensor when the information is the second information.

According to various embodiments of the present disclosure, the operation of receiving the information corresponding to the application may include: receiving the information corresponding to the application based on at least some of a situation of a physical separation from the electronic device 500.

According to various embodiments of the present disclosure, the operation of obtaining the data corresponding to the activated sensor may include: obtaining the first data or the second data, which includes biometric data.

According to various embodiments of the present disclosure, the operation of transmitting the obtained data to the electronic device 500 may include: transmitting the data to the electronic device 500 based on at least some of a situation of a contact with a touch screen included in the electronic device 500.

According to various embodiments of the present disclosure, the operation of receiving the information corresponding to the application may include: receiving, as the information, a request for the first data corresponding to a first application when the application is the first application; and receiving, as the information, a request for the second data corresponding to a second application when the application is the second application.

According to various embodiments of the present disclosure, the operation of transmitting the obtained data to the electronic device 500 may include: transmitting the data to the electronic device 500 so that biometric information corresponding to the data is displayed through a display included in the electronic device 500.

According to various embodiments of the present disclosure, the external electronic device 600 is an accessory device of the electronic device 500 that includes the stylus pen 410.

According to various embodiments of the present disclosure, there is provided a storage device that stores instructions. The instructions are configured to enable at least one processor to execute at least one operation when the instructions are executed by the at least one processor, and the at least one operation includes: receiving, by an electronic device (e.g., the external electronic device 600) including a first sensor, a second sensor, and a communication interface, information corresponding to an application that is executed in an external electronic device, from an external electronic device (e.g., the electronic device 500) through the communication interface; when the information is first information, activating the first sensor and deactivating the second sensor; when the information is second information, deactivating the first sensor and activating the second sensor; by using an activated sensor out of the first sensor and the second sensor, obtaining data corresponding to the activated sensor out of the first data and the second data; and transmitting the obtained data to the external electronic device.

According to various embodiments of the present disclosure, there is provided a storage device that stores instructions. The instructions are configured to enable at least one processor to execute at least one operation when the instructions are executed by the at least one processor, and the at least one operation includes: receiving, by an electronic device (e.g., the external electronic device 600) including a first sensor, a second sensor, and a communication interface, information corresponding to an application that is executed in an electronic device (e.g., the electronic device 500) that is functionally connected with the accessory device, from the electronic device (e.g., the electronic device 500) through the communication interface; when the information is first information, obtaining first data through the first sensor; when the information is second information, obtaining second data through the second sensor; and transmitting, to the electronic device, data obtained out of the first data and the second data.

According to various embodiments of the present disclosure, there is provided a storage device that stores instructions. The instructions are configured to enable at least one processor to execute at least one operation when the instructions are executed by the at least one processor, and the at least one operation includes: determining, by an electronic device (e.g., the electronic device 500) that includes a communication interface, an application executed in the electronic device; when the application is a first application, transmitting first information corresponding to the first application to an accessory device that includes a first sensor and a second sensor, through the communication interface; when the application is a second application, transmitting second information corresponding to the second application to the accessory device through the communication interface; and receiving, from the accessory device, data obtained through a sensor out of the first sensor or the second sensor, which corresponds to information transmitted from among the first information and the second information.

Embodiments of the present disclosure provided in the present specifications and drawings are merely certain examples to readily describe the technology associated with embodiments of the present disclosure and to help understanding of the embodiments of the present disclosure, but may not limit the embodiments of the present disclosure. Therefore, in addition to the embodiments disclosed herein, the various embodiments of the present disclosure should be construed to include all modifications or modified forms drawn based on the technical idea of the various embodiments of the present disclosure.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

The control unit may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for". In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

What is claimed is:

1. An electronic pen, comprising:
   a wireless communication circuit;
   a first biometric sensor and a second biometric sensor; a power supplying unit configured to supply power for an operation of the electronic pen; and
   at least one processor electrically connected to the wireless communication circuit and the power supplying unit, the at least one processor configured to:
   in response to detecting detachment from a mobile device, activate the wireless communication circuit to initiate short-range wireless communication, and
   control the wireless communication circuit to establish communication with the mobile device via the short-range wireless communication,
   receiving a request for biometric data from the mobile device, and determining whether to activate the first biometric sensor or the second biometric sensor based on information included in the request indicating an association of executed application with the first biometric sensor or the second biometric sensor,
   wherein power is received from the mobile device to charge the power supplying unit of the electronic pen based on at least one of a state in which the electronic pen is inserted into the mobile device or a state in which the electronic pen is attached to a specific area of the mobile device.

2. The electronic pen of claim 1, further comprising:
   at least one of a gesture sensor, an acceleration sensor or a gyro sensor.

3. The electronic pen of claim 2, wherein the at least one processor is further configured to:
   obtain information using the at least one of the gesture sensor, the acceleration sensor or the gyro sensor; and
   control the wireless communication circuit to transmit the obtained information to the mobile device.

4. The electronic pen of claim 1, further comprising:
   a first biometric sensor configured to obtain first biometric data; and
   a second biometric sensor configured to obtain second biometric data.

5. The electronic pen of claim 4, wherein determining whether to activate the first biometric sensor or the second biometric sensor includes:
   after the communication with the mobile device is established, receive, from the mobile device, the request for biometric data, the request corresponding to the executed application of the mobile device;
   in response to identifying that the first biometric sensor corresponds to the executed application, activating the identified first biometric sensor without activating the second biometric sensor; and
   in response to identifying that the second biometric sensor corresponds to the executed application, activating the identified second biometric sensor without activating the first biometric sensor;
   obtain the biometric data through the first biometric sensor; and
   control the wireless communication circuit to transmit the biometric data to the mobile device.

6. The electronic pen of claim 4, wherein the first or second biometric data is transmitted to the mobile device in response to detecting contact of the electronic pen to a touch screen of the mobile device.

7. The electronic pen of claim 6, wherein the second biometric sensor is associated with another inactive application of the mobile device, and the second biometric sensor is deactivated when the first biometric sensor is activated.

8. The electronic pen of claim 1, further comprising:
at least one of a display or an indicator for indicating a battery charging state of the power supplying unit.

9. A mobile device, comprising:
a wireless communication circuit;
a display;
a housing defining an opening for stowing an electronic pen; and
at least one processor electrically connected to the wireless communication circuit and the display, the at least one processor configured to:
detect detachment of the electronic pen,
in response to detecting the detachment of the electronic pen, control the wireless communication circuit to establish short-range wireless communication with the electronic pen, and
transmit a request for biometric data to the electronic pen, wherein the electronic pen determines whether to activate a first biometric sensor or a second biometric sensor of the electronic pen, based on information included in the request indicating an association of an executed application with the first biometric sensor or the second biometric sensor,
wherein power is provided to the electronic pen to charge a power supplying unit of the electronic pen based on at least one of a state in which the electronic pen is inserted into the mobile device or a state in which the electronic pen is attached to a specific area of the mobile device, and
wherein the power supplying unit of the electronic pen is configured to supply power for an operation of the electronic pen.

10. The mobile device of claim 9, wherein the at least one processor is configured to:
control the display to display an indication of a battery charging state of the electronic pen.

11. The mobile device of claim 9, wherein the at least one processor is configured to:
control the wireless communication circuit to receive, from the electronic pen, information obtained by at least one sensor included in the electronic pen; and
control an application executing in the mobile device based on the received information.

12. The mobile device of claim 9, wherein the at least one processor is configured to:
identify a first application executed in the mobile device;
after the electronic pen is detached from the mobile device, control the wireless communication circuit to transmit to the electronic pen, information requesting biometric data corresponding to the first application executed in the mobile device; and
control the wireless communication circuit to receive, from the electronic pen, biometric data obtained by at least one sensor included in the electronic pen.

13. The mobile device of claim 12, further comprising a touch screen, wherein the at least one processor is configured to:
in response to detecting a contact of the electronic pen to the touch screen, display the biometric data at a position of the contact on the touch screen.

14. A method in an electronic pen, comprising:
detecting, by at least one processor, detachment of the electronic pen from a mobile device in which the electronic pen is stowable;
in response to detecting the detachment, activating a wireless communication circuit of the electronic pen to initiate short-range wireless communication;
establishing communication with the mobile device via the short-range wireless communication;
after establishing communication with the mobile device, receiving from the mobile device a request for biometric data corresponding to an application executed in the mobile device;
in response to receiving the request, identifying whether a first biometric sensor corresponds to the executed application from among the first biometric sensor and a second biometric sensor, based on information included in the request;
determine whether to activate the first biometric sensor or the second biometric sensor of the electronic pen based in the identification, including;
in response to identifying that the first biometric sensor corresponds to the executed application, activation the identified first biometric sensor without activating the second biometric sensor, and
in response to identifying that the second biometric sensor corresponds to the executed application, activating the identified second biometric sensor without activating the first biometric sensor;
obtaining the biometric data through the first biometric sensor; and
transmitting the biometric data to the mobile device.

15. The method of claim 14, further comprising:
obtaining information using at least one of a gesture sensor, an acceleration sensor, or a gyro sensor included in the electronic pen; and
transmitting the obtained information to the mobile device.

16. The method of claim 1, further comprising, transmitting the biometric data to the mobile device in response to detecting contact of the electronic pen to a touch screen of the mobile device.

* * * * *